United States Patent [19]

Meanwell et al.

[11] Patent Number: 4,701,459
[45] Date of Patent: Oct. 20, 1987

[54] 7-AMINO-1,3-DIHYDRO-2H-IMIDAZO[4,5-B]QUINOLIN 2-ONES AND METHOD FOR INHIBITING PHOSPHODIESTERASE AND BLOOD PLATELET AGGREGATION

[75] Inventors: Nicholas A. Meanwell, Mt. Vernon; John J. Wright, Evansville, both of Ind.

[73] Assignee: Bristol-Myers Company, New York, N.Y.

[21] Appl. No.: 883,258

[22] Filed: Jul. 8, 1986

[51] Int. Cl.$^4$ .................. A61K 31/47; C07D 471/04
[52] U.S. Cl. .................. 514/293; 514/235; 514/254; 546/82; 544/126; 544/361
[58] Field of Search ............ 544/126, 361; 514/293, 514/254, 235; 546/82

[56] References Cited

U.S. PATENT DOCUMENTS 3,932,407  1/1976  Beverung, Jr. et al. ............ 544/250
4,256,748  3/1981  Chodnekar et al. ................ 514/267
4,490,371 12/1984  Jones et al. ...................... 514/234

FOREIGN PATENT DOCUMENTS 129258 12/1984 European Pat. Off. .
133234  2/1985 European Pat. Off. .
153152  8/1985 European Pat. Off. .

OTHER PUBLICATIONS

Kozak et al., *Bull. Intern. Acad. Polanaise*, 1930A, 432–438 (Chem. Abs., 25, 5400).
Musial, *Roczniki Chem.*, 1951, 25, 46–52 (Chem. Abs., 1953, 47, 4885f).
Fryer et al., *J. Org. Chem.*, 1977, 42, 2212–2219.
Reid et al., *Chem. Ber.*, 1956, 89, 2684–2687.
Fleming et al., *New Drugs Annual: Cardiovascular Drugs*, Raven Press, pp. 277–294, New York (1983).
Ishikawa et al, *J. Med. Chem.*, 28, 1387–1393 (1985).

Primary Examiner—Henry R. Jiles
Assistant Examiner—Zinna Northington
Attorney, Agent, or Firm—Robert H. Uloth

[57] ABSTRACT

Novel series of 2,3-dihydro-2-oxo-1H-imidazo[4,5-b]quinolinyl amine derivatives of Formula

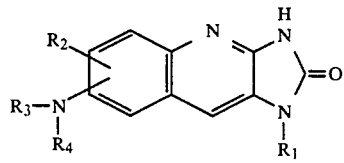

wherein $R_1$ is hydrogen, lower alkyl; $R_2$ is hydrogen, lower alkyl, lower alkoxy, halogen; $R_3$ is hydrogen, lower alkyl; $R_4$ is hydrogen, lower alkyl, alkanoyl, phenylalkanoyl wherein phenyl is optionally substituted with halogen, lower alkyl, lower alkoxy; $R_3$ and $R_4$ are joined together to form morpholinyl, piperidinyl or pyrrolidinyl optionally substituted with —$CO_2R_5$ or

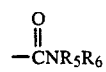

wherein $R_5$ is hydrogen or lower alkyl, and $R_6$ is hydrogen, lower alkyl, cycloalkyl; 4-$R_7$-piperazinyl wherein $R_7$ is —$CO_2R_8$ wherein $R_8$ is lower alkyl, phenyl optionally substituted with up to 2 halogen, lower alkyl or lower alkoxy; phenylalkanoyl of 7 to 10 carbon wherein phenyl is unsubstituted or independently substituted with up to 2 halogen, lower alkyl, lower alkoxy. The compounds are cyclic AMP phosphodiesterase inhibitors and are particularly useful as inhibitors of blood platelet aggregation and/or as cardiotonic agents.

20 Claims, No Drawings

7-AMINO-1,3-DIHYDRO-2H-IMIDAZO[4,5-B]QUINOLIN 2-ONES AND METHOD FOR INHIBITING PHOSPHODIESTERASE AND BLOOD PLATELET AGGREGATION

BACKGROUND OF THE INVENTION

This invention generally pertains to heterocyclic carbon compounds having drug and bio-affecting properties and to their preparation and use. In particular, the invention is concerned with a series of new 2,3-dihydro-2-oxo-1H-imidazo[4,5-b]quinolinylamine derivatives which are phosphodiesterase inhibitors, blood platelet antiaggregators and cardiotonic agents. According to conventional nomenclature, the basic heterocyclic structure can be referred to as 1,3-dihydro-2H-imidazo[4,5-b]quinolin-2-one.

As a structural class, relatively few 1,3-dihydro-2H-imidazo[4,5-b]quinolin-2-ones are known to applicants with the following chemical literature illustrative of the art.

Kozak, et al., *Bull. Intern. Acad. Polanaise*, 1930A, 432–438 (Chem. Abs., 25, 5400) describes the unsubstituted compound 1,3-dihydro-2H-imidazo[4,5-b]quinolin-2-one of formula (i).

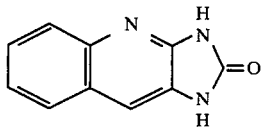

(i)

Musial, *Roczniki Chem.*, 1951, 25, 46–52 (Chem. Abs., 1953, 47, 4885f) synthesized 1,3-derivatives of (i) as illustrated in formula (ii).

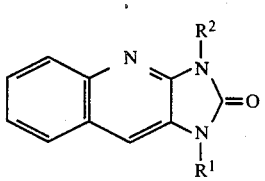

(ii)

$R^1$ = Br, $NO_2$, $NH_2$
$R^2$ = H, Br

Fryer, et al., *J. Org. Chem.*, 1977, 42, 2212–2219 describes the 3,7,9-trisubstituted compound of formula (iii).

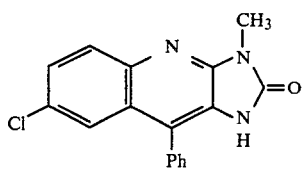

(iii)

Reid, et al., *Chem. Ber.*, 1956, 89, 2684–2687 describes the synthesis of the 1,3-diphenyl derivative of formula (iv).

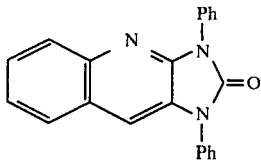

(iv)

No pharmacological utility is taught for the 1,3-dihydro-2H-imidazo[4,5-b]quinolin-2-one structures disclosed in the aforementioned references which are of a chemical nature.

Various derivatives of the tetrahydroimidazo[2,1-b]quinazolin-2-one (v) heterocycle have been studied for their platelet inhibition and cardiotonic properties.

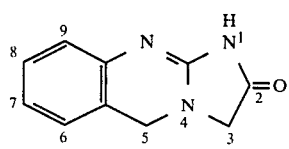

(v)

For example:

Beverung, Jr., et al., U.S. Pat. No. 3,932,407 disclose a series of compounds useful as blood platelet antiaggregative and/or antihypertensive and/or bronchodilator agents of the tetrahydroimidazo[2,1-b]quinazolin-2-one class. Anagrelide (vi), a particularly preferred member of the Beverung, Jr., et al. series, has been studied extensively, e.g., J. S. Fleming, et al., *New Drugs Annual: Cardiovascular Drugs*, Raven Press, pages 277–294, New York (1983).

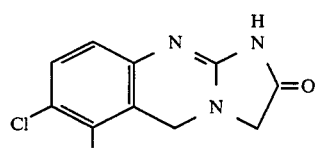

(vi)

Chodnekar, et al, U.S. Pat. No. 4,256,748 describes a series of tetrahydroimidazo[2,1-b]quinazolin-2-ones of the formula (vii) as inhibitors of the aggregation of blood platelets and cardiotonic activity.

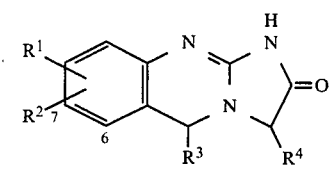

(vii)

Representative of the Chodneker compounds are RO 15-2041 ($R^4$=$CH_3$, $R^3$=H, $R^2$=6—$CH_3$, $R^1$=7—Br) and RO 13-6438 ($R^4$=$CH_3$, $R^3$=H, $R^2$=6—$CH_3$, $R^1$=H).

Jones, et al., U.S. Pat. No. 4,490,371 describes another series of tetrahydroimidazo[2,1-b]quinazolin-2-one derivatives as cyclic AMP phosphodiesterase inhibitors useful as thrombogenic agents. Among the compounds disclosed is the formula (viii) amide, identified in the art as RS82856.

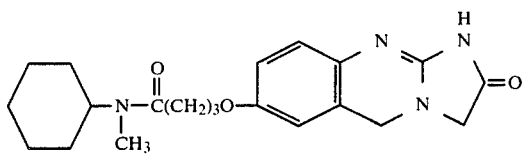
(viii)

Fried, et al., European Patent Application No. 153152 further describes tetrahydroimidazo[2,1-b]quinozolin-2-ones of formula (ix) as cyclic AMP phosphodiesterase inhibitors useful as antithrombogenic agents.

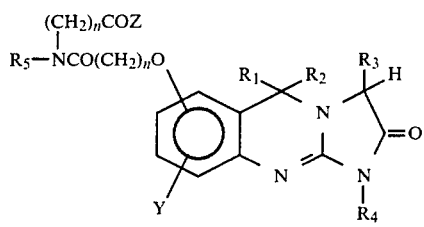
(ix)

F. Ishikawa, et al., *J. Med. Chem.*, 28, 1387–1393 (1985) describe amino substituted 1,2,3,5-tetrahydroimidazo[2,1-b]quinazolin-2-one compounds having blood platelet aggregation inhibitor activity of formula (x) wherein $R_1$ is dialkylamino, cyclic amino (e.g., piperidino) and $R_2$ represents hydrogen, halogen, alkyl, alkoxy. Published European patent application Nos. 129,258 and 133,234 cover this subject matter.

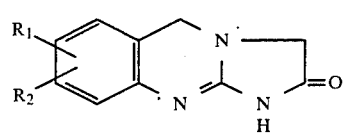
(x)

SUMMARY OF THE INVENTION

In its broadest aspect, this invention is concerned with a new series of 2,3-dihydro-2-oxo-imidazo[4,5-b]quinolinylamine derivatives having valuable pharmacological properties which makes them particularly useful as cardiotonic agents and/or inhibitors of phosphodiesterase and mammalian blood platelet aggregation. Formula I illustrates the compounds of the invention and the ring numbering system used herein.

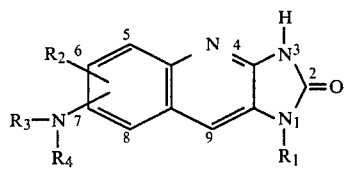
(I)

In the foregoing formula:
$R_1$ is hydrogen, lower alkyl;
$R_2$ is hydrogen, lower alkyl, lower alkoxy, halogen;
$R_3$ is hydrogen, lower alkyl;
$R_4$ is hydrogen, lower alkyl, alkanoyl of 1 to 6 carbon atoms, phenylalkanoyl of 7 to 10 carbon wherein phenyl is optionally substituted with halogen, lower alkyl, or lower alkoxy;

$R_3$ and $R_4$ are joined together to form morpholinyl, piperidinyl or pyrrolidinyl optionally substituted with —$CO_2R_5$ or

wherein $R_5$ is hydrogen or lower alkyl, and $R_6$ is hydrogen, lower alkyl, cycloalkyl of 5 to 7 carbon atoms; 4-$R_7$-piperazinyl wherein $R_7$ is —$CO_2R_8$ wherein $R_8$ is lower alkyl, phenyl optionally substituted with up to 2 halogen, lower alkyl or lower alkoxy; phenylalkanoyl of 7 to 10 carbon atoms wherein phenyl is unsubstituted or independently substituted with up to 2 halogen, lower alkyl, lower alkoxy.

Another embodiment of the invention relates to pharmaceutically acceptable compositions comprised of a Formula I compound or a pharmaceutically acceptable salt thereof combined with at least one pharmaceutically acceptable excipient. A further embodiment of this invention relates to a method for inhibiting phosphodiesterase and blood platelet aggregation in a mammal which comprises administering a therapeutically effective amount of a compound of Formula I or a pharmaceutically acceptable salt thereof to a mammal in need of such treatment. A still further embodiment of this invention relates to a method for increasing heart inotropic activity which comprises administering a therapeutically effective amount of a compound of Formula I or a pharmaceutically acceptable salt thereof to a mammal in need of such treatment.

DETAILED DESCRIPTION OF THE INVENTION

The compounds of the instant invention comprise those of Formula I

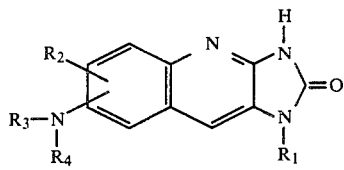
(I)

wherein
$R_1$ is hydrogen, lower alkyl;
$R_2$ is hydrogen, lower alkyl, lower alkoxy, halogen;
$R_3$ is hydrogen, lower alkyl;
$R_4$ is hydrogen, lower alkyl, alkanoyl of 1 to 6 carbon atoms, phenylalkanoyl of 7 to 10 carbon atoms wherein phenyl is optionally substituted with halogen, lower alkyl, or lower alkoxy;
$R_3$ and $R_4$ are joined together to form morpholinyl, piperidinyl or pyrrolidinyl optionally substituted with —$CO_2R_5$ or

wherein
$R_5$ is hydrogen or lower alkyl, and $R_6$ is hydrogen, lower alkyl, cycloalkyl of 5 to 7 carbon atoms; 4-$R_7$-piperazinyl wherein $R_7$ is —$CO_2R_8$ wherein $R_8$ is lower alkyl, phenyl optionally substituted with up to 2 halogen, lower alkyl or lower alkoxy; phenylalkanoyl of 7 to 10 carbon wherein phenyl is unsubstituted or independently substituted with up to 2 halogen, lower alkyl, lower alkoxy;

or a pharmaceutically acceptable salt thereof.

It is understood that as used herein limitations of Formula I are defined as follows:

The term "halogen" or "halo" comprehends fluorine, iodine, and most preferably bromine and chlorine.

The term "lower alkyl" refers to a branched or unbranched saturated hydrocarbon chain containing from 1 to 4 carbon atoms; specifically, methyl, ethyl, n-propyl, isopropyl, n-butyl, secondary butyl and tert.-butyl. The terms "alkyl of 1 to 4 carbon atoms" and "lower alkyl" are used interchangeably and specific terms may be represented by conventional symbols, i.e., Me=$CH_3$, Et=$C_2H_5$, etc.

The term "lower alkoxy" comprehends ethers containing from 1 to 4 carbon atoms as defined for alkyl; such as methoxy, ethoxy, isopropoxy, tert.-butoxy, and the like.

The term "alkanoyl of 1–6 carbon atoms" comprehends both unbranched or branched aliphatic acids such as, for example, formic acid, acetic acid, propanoic acid, butyric acid, pentanoic acid, hexanoic acid or any isomer of these acids which has up to 6 carbons atoms and is fully saturated.

The term "phenylalkanoyl" of 7 to 10 carbon atoms comprehends benzoic acid, phenylacetic acid, 3-phenylpropanoic acid, 4-phenylbutyric acid, 2-phenylpropanoic acid, and the like.

According to the present invention, the compounds characterized by Formula I and the pharmaceutically acceptable acid addition salts thereof are obtained by a process comprising (a) reducing a substituted hydantoin of Formula II

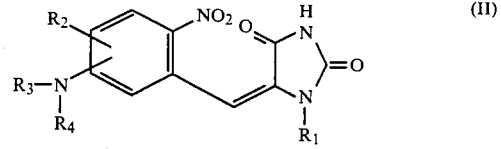

(II)

wherein $R_1$, $R_2$, $R_3$ and $R_4$ are defined as above;

(b) treating the reduced material with an oxidant such as iodine when required; or (c) hydrolyzing a compound of Formula $I^a$

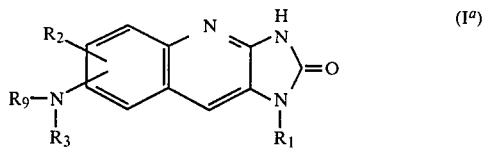

($I^a$)

wherein $R_1$, $R_2$ and $R_3$ are defined as above and $R_9$ is alkanoyl of 1 to 6 carbon atoms to the Formula I amino derivative wherein $R_4$ is hydrogen; and (d) converting the free base of a compound of Formula I to a pharmaceutically acceptable acid addition salt when desired.

The reduction of Formula II hydantoin intermediates is carried out by conventional chemical or catalytic methods. For instance, the Formula II hydantoins can be chemically reduced by treatment with hydrogen iodide and red phosphorus according to the method of Kozak, et al., supra. Catalytic hydrogenation is particularly preferred and accomplished with a transition metal catalyst, preferably palladium-on-carbon, in an appropriate reaction inert solvent such as dimethylformamide (DMF). Reduction is carried out at room temperature and when hydrogen uptake is essentially complete, the reaction mixture is warmed and filtered or optionally heated to about 100° C. for a 1 to 4 hour period before filtering. In some instances, residual material (obtained by concentrating the filtrate) predominantly consists of the desired Formula I product produced by facile cyclization and aromatization to the fused quinoline ring system. In other instances, the residual material predominantly consists of the uncyclized Formula $II^a$ aniline derivative

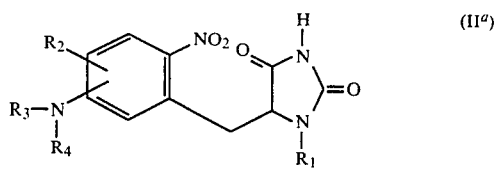

($II^a$)

wherein $R_1$, $R_2$, $R_3$ and $R_4$ are as defined above or the 1,3,9,9a-tetrahydroquinoline intermediate of Formula $II^b$ resulting from cyclization of $II^a$,

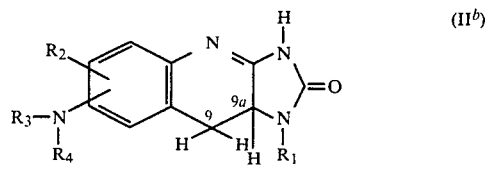

($II^b$)

wherein $R_1$, $R_2$, $R_3$ and $R_4$ are defined as above. In other instances, the residual material predominantly consists of a mixture of Formula $II^a$, $II^b$ intermediates together with the desired Formula I product. Without being bound by theory, the transformation of a Formula II nitro-hydantoin to the Formula I product is thought to involve reduction of the nitro group and olefenic double bond to the corresponding Formula $II^a$ aniline. Ring cyclization follows or occurs simultaneously to the Formula I product or the 1,3,9,9a-tetrahydroquinoline intermediate of Formula $II^b$ which is aromatized by dehydrogenation. In those cases where reaction is incomplete, the residual material is treated with an oxidant such as iodine in an alkanol solvent such as methanol or an inert solvent such a dimethylformamide, acetonitrile and the like at reflux temperature. Under these conditions, cyclization of Formula $II^a$ anilines to the Formula $II^b$ tetrahydroquinoline intermediates with oxidation of the latter to the desired 2,3-dihydro-2oxo-1H-imidazo[4,5-b]quinolinylamine derivatives of Formula I is effected. The Formula $II^a$ and $II^b$ compounds along with the Formula II nitrohydantoins are considered part of the instant invention. When iodine is employed, the Formula I product is isolated in base form by treating the reaction mixture with aqueous sodium thiosulfate and alkali metal carbonate such as sodium carbonate.

In the case of Formula II compounds containing an ester grouping (e.g., $R_5$ of $CO_2R_5$ is lower alkyl) ester interchange can take place whenever an alkanol solvent is employed in the oxidation step. For instance, when methanol is used and "$R_5$" is not methyl, the Formula I product can consist of a mixture of the "$R_5$" and methyl esters with the latter generally predominating. The esters of Formula II (i.e., $R_5$ of $-CO_2R_5$ is lower alkyl) are conventionally converted to corresponding acids by base hydrolysis. In the case of Formula II compounds containing an acid grouping (i.e., $R_5$ of $-CO_2R_5$ is hydrogen) esterification can take place under the relative acid conditions of the oxidation step.

With reference to the above process "(d) converting the free base of a compound of Formula I to a pharmceutically acceptable acid addition salt thereof", conventional methods are used. For instance, pharmaceutically acceptable salts of Formula I are obtained by treating a Formula I base with the selected acid preferably in solution. They may also be made by metathesis or treatment with an ion exchange resin under conditions in which the anion of one salt of the substance of the Formula I is replaced by another anion under conditions which allow for separation of the desired species such as by precipitation from solution or extraction into a solvent, or elution from or retention on an ion exchange resin. The pharmaceutically acceptable acid addition salts of the instant invention are those in which the anion does not contribute significantly to the toxicity or pharmacological activity of the salt and, as such, they are the pharmacological equivalents of the bases of Formula I. They are generally preferred for medical usage. In some instances, they have physical properties which make them more desirable for pharmaceutical formulation purposes such as solubility, lack of hygroscopicity, compressibility with respect to tablet formation and compatibility with other ingredients with which the substance may be used for pharmaceutical purposes. Pharmaceutically acceptable acids for the purposes of salt formation of the substances of Formula I include hydrochloric, hydrobromic, hydroiodic, citric, acetic, propionic, benzoic, mandelic, sulfuric, phosphoric, nitric, mucic, isethionic, methanesulfonic, ethanesulfonic, p-toluene sulfonic, palmitic, heptanoic, and others.

The Formula II hydantoins employed in the process for preparing compounds of Formula I can be prepared according to procedures described by Billek, Montash, 1961, 92, 352–360 (Chem. Abs., 1962, 56, 394b) illustrated in the following reaction scheme.

Method A of the N-acetyl intermediate (V) obtained in Step 1 is conventionally carried out with an alkali metal hydroxide such as sodium hydroxide to provide the benzylidine hydantoin of Formula II.

An alternate and preferred method for preparing Formula II hydantoins involves reaction of the 2-nitrobenzaldehyde of Formula III with a hydantoin-5-phosphonate of Formula VI (wherein $R_1$ is hydrogen or lower alkyl) illustrated in the following reaction scheme.

METHOD B

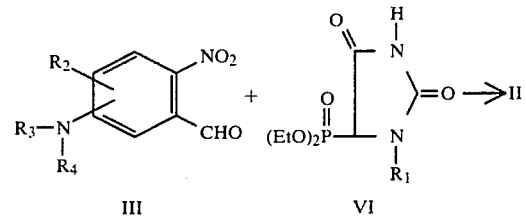

The reaction is conveniently carried out at room temperature by adding the phosphonate (VI) to a molar equivalent of sodium dissolved in an alkanol solvent such as ethanol followed by addition of the benzaldehyde (III). Alternatively, phosphonate (VI) can be added to an organic base such as triethylamine in a solvent such as acetonitrile at room temperature. A relatively short period of time is required to complete the reaction (e.g. 0.5 to 2 hours) and the hydantoin (II) is isolated by concentrating the reaction mixture and washing the residue with water. The benzylidine hydantoin derivatives (II) thus obtained frequently consist of a mixture of geometrical isomers wherein the predominant isomer has the vinyl proton (where present) resonating at lower field in the NMR spectrum. In the instant process for preparing Formula I compounds from hydantoins (II), it is immaterial as to which isomer is used since the double bond is reduced.

The Formula (VI) phosphonates are prepared by brominating the appropriate $R_1$-imidazolidine-2,4-dione and coupling the product with triethylphosphite as set forth in the following typical preparation of diethyl

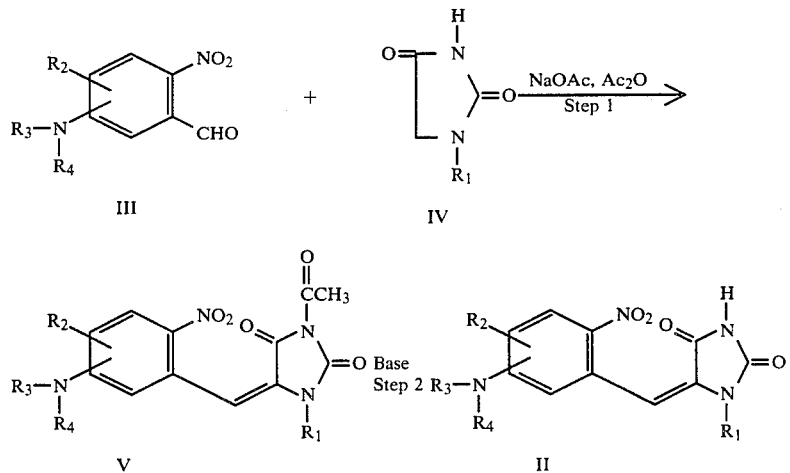

Method A involves condensation of a substituted benzaldehyde of Formula II with hydantoin (IV) in the presence of fused sodium acetate in acetic anhydride at elevated temperatures (e.g., 100°–160° C.). Hydrolysis 1-methyl-2,4-dioxoimidazolidine-5-phosphonate and analogs.

A mixture of 1-methylimidazolidine-2,4-dione (202.5 g, 1.8M) and glacial acetic acid (1L) was heated to 90° C. in an oil bath. An addition funnel was charged with bromine (311.5 g, 100 mL, 1.95M) and a small amount of bromine introduced into the reaction mixture. After dissipation of the orange color, the remainder of the bromine was added dropwise at such a rate that instant decolorization occurred. After completing the addition, the mixture was stirred at 90° C. for 60 minutes, cooled to room temperature and stirred overnight. The acetic acid was decanted from a white precipitate, concentrated in vacuo and the residue combined with the precipitate and suspended in diethyl ether (approximately 2L). Triethyl phosphite (295 g, 320 mL, 1.8M) was added portionwise with stirring. An exothermic reaction ensued which was controlled with tap water cooling of the reaction vessel. A solution resulted which, on continued stirring, yielded a white precipitate. After standing for 60 minutes the mixture was poured into diethyl ether (4L) and allowed to stand overnight. Filtration afforded diethyl-1-methyl-2,4-dioxoimidazolidine-5-phosphonate (331.7 g, 75%), m.p. 95°–96° C. An analytical sample crystallized from MeOH/Et$_2$O had m.p. 95°–95° C.

Anal. Calcd. for $C_8H_{15}N_2O_5P$: C, 38.41; H, 6.04; N, 11.20. Found: 38.22; H, 6.07; N, 11.04.

The following 5-phosphonate hydantoin intermediates can be prepared analogously by substituting the appropriate imidazolidine-2,4-dione for 1-methylimidazolidine-2,4-dione in the above procedure:

diethyl 2,4-dioxoimidazolidine-5-phosphonate, m.p. 161°–163° C. crystallized from ethanol,
diethyl 1-ethyl-2,4-dioxoimidazolidine-5-phosphonate,
diethyl 1-propyl-2,4-dioxoimidazolidine-5-phosphonate,
diethyl 1-isopropyl-2,4-dioxoimidazolidine-5-phosphonate,
diethyl 1-butyl-2,4-dioxoimidazolidine-5-phosphonate,
diethyl 1-iso-butyl-2,4-dioxoimidazolidine-5-phosphonate,
diethyl 1-tert-butyl-2,4-dioxoimidazolidine-5-phosphonate.

Requisite aldehyde intermediates III (compound (6)) are obtained by conventional methods as illustrated in the following reaction schemes:

Scheme 1

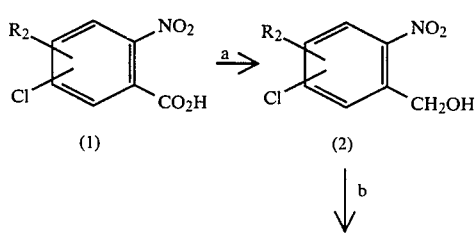

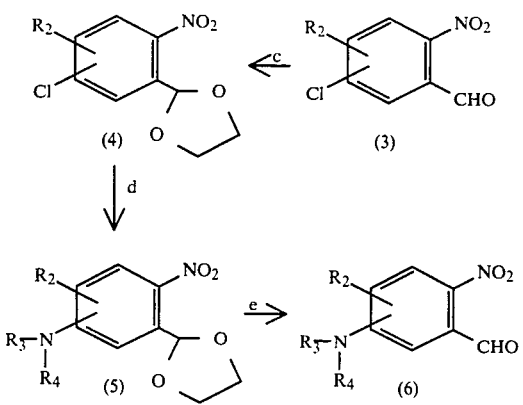

Reagents: a. BH$_3$/THF
b. pyridinium chlorochromate
c. HOCH$_2$CH$_2$OH/H$^+$
d. R$_3$R$_4$NH
e. THF/H$^+$ In Scheme 1, the benzyl alcohol (2), obtained by reducing benzoic acid (1) with borane/tetrahydrofuran (THF) complex, is oxidized to aldehyde (3) with pyridinium chlorochromate in dichloromethane. Acetal (dioxolane) derivative (4), formed with ethylene glycol in an inert solvent such as benzene under acid (e.g., p-toluenesulfonic acid) conditions to protect the aldehyde group, is heated with the appropriate R$_3$R$_4$NH amine to provide the dioxolane intermediate (5) which is hydrolyzed with acid to benzaldehyde (6). In the case wherein R$_2$ is halogen, another step carried out by conventional crystallization or chromatography laboratory techniques may be required in order to separate different positional amine intermediates (5) which can result in step (d) during R$_3$R$_4$NH function. Examples of benzaldehydes prepared by this scheme are:

2-nitro-5-(1-piperidinyl)benzaldehyde, m.p. 102°–103° C., 2-nitro-5-(1-pyrrolidinyl)benzaldehyde, m.p. 128°–129° C., 2-nitro-5-diethylaminobenzaldehyde, 2-nitro-5-(4-ethoxycarbonyl-1-piperidinyl)benzaldehyde, 2-nitro-5-(4-morpholinyl)benzaldehyde, m.p. 166°–168° C., 2-nitro-5-(4-phenyl-1-piperazinyl)benzaldehyde.

Scheme 2

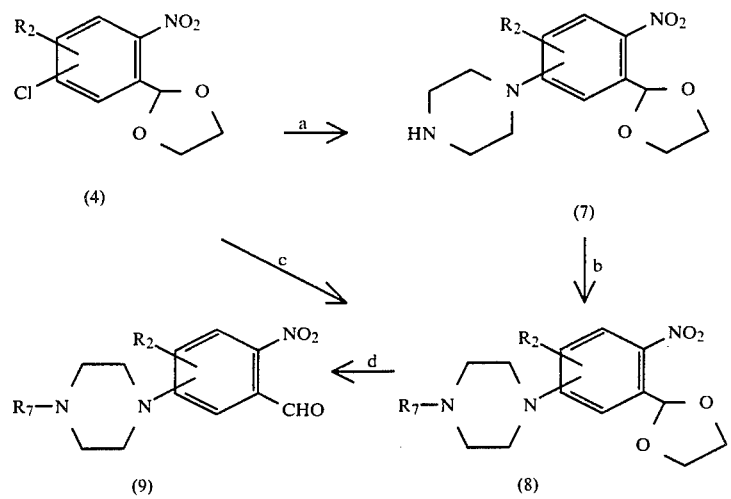

(4) (7) (8) (9)

Reagents: a. piperazine
b. R$_8$CO$_2$Cl;
phenylalkanoyl chloride
c. phenylpiperazine
d. THF/H$^+$ In Scheme 2, dioxolane (4) is heated with an excess of piperazine to afford (7) which is derivatized with an appropriate R$_8$CO$_2$Cl (e.g., ethyl chloroformate) or phenylalkanoyl chloride (e.g., phenylacetyl chloride) thus providing the R$_7$-substituted piperazinyl intermediate (8) wherein R$_7$ is as defined herein. Alternatively, the R$_7$-piperazinyl intermediate (8) can be prepared by reacting dioxolane (4) directly with the appropriate R$_7$-piperazine. Hydrolysis of R$_7$-piperazinyl intermediate (8), carried out in tetrahydrofuran under acidic conditions, affords the aldehyde (9).

In the case of dioxolane (4) wherein R$_2$ is halogen, another step may be required in order to separate different amino position isomers which can result in steps (a) or (c) during fusion with piperazine or R$_7$-piperazine. Such separations are conventionally carried out employing standard crystallization and chromatography techniques. Examples of benzaldehydes prepared by this scheme are:

2-nitro-5-(4-ethoxycarbonyl-1-piperazinyl)benzaldehyde, m.p. 136°–137° C.,
2-nitro-5-(4-benzoyl-1-piperazinyl)benzaldehyde,
2-nitro-5-[4-(3,4-dimethoxybenzoyl)-1-piperazinyl]benzaldehyde, m.p. 200°–201° C.

Scheme 3

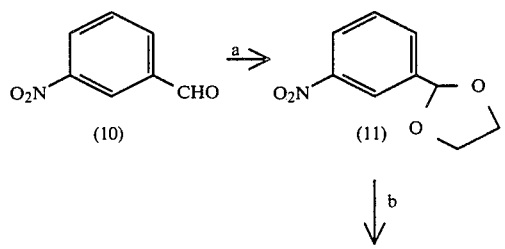

(10) (11)

-continued

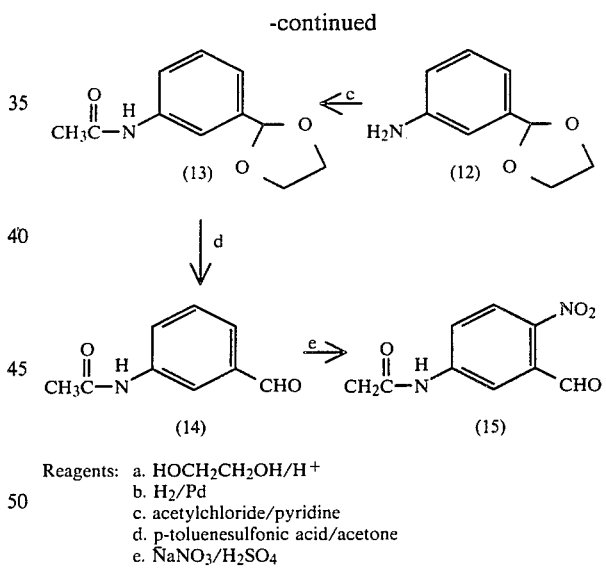

(13) (12)

(14) (15)

Reagents: a. HOCH$_2$CH$_2$OH/H$^+$
b. H$_2$/Pd
c. acetylchloride/pyridine
d. p-toluenesulfonic acid/acetone
e. NaNO$_3$/H$_2$SO$_4$ In Scheme 3, 3-nitrobenzaldehyde (10), protected by forming dioxolane (11) with ethylene glycol, is reduced catalytically to the aniline intermediate (12). Acylation of (12) with acetyl chloride in pyridine affords acetamide (13) with benzaldehyde (14) obtained by acid hydrolysis of the dioxolane protecting group. Nitration of (14) affords 2-nitrobenzaldehyde (15). Analogous 2-nitrobenzaldehydes can be obtained by substituting appropriate alkanoyl halides for acetyl chloride in step (c). Examples of benzaldehydes prepared by this scheme are:
2-nitro-5-acetamidobenzaldehyde,
2-nitro-5-propionamidobenzaldehyde,
2-nitro-5-(2-methylpropionamido)benzaldehyde.

Scheme 4

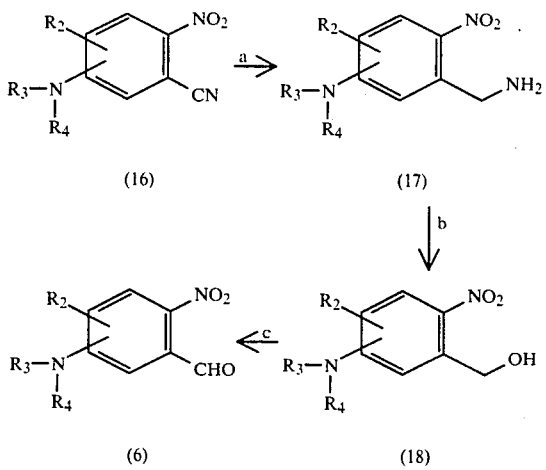

(16) (17) (6) (18)

Reagents:
a. NaBH$_4$/F$_3$CO$_2$H/THF
b. (1) NaNO$_2$/CH$_3$CO$_2$H/H$_2$O
   (2) NaOH
c. pyridinium chlorochromate In Scheme 4, the nitrile (16) and corresponding benzylamine (17) starting materials are obtained as described by F. Ishikawa, *J. Med. Chem.*, 28, 1387–1393 (1985). Conversion of benzylamine (17) to the corresponding benzyl alcohol (18) is carried out by conventional methods, e.g. treatment of the amine with sodium nitrite in acetic acid and water followed by base treatment to hydrolyze the acetic acid ester (if present) of (18). Oxidation of the benzyl alcohol (18) with pyridinium chlorochromate in dichloromethane affords the benzaldehyde (6). Examples of benzaldehydes prepared by this method are:
2-nitro-5-dimethylamino-6-chlorobenzaldehyde,
2-nitro-5-diethylamino-6-chlorobenzaldehyde,
2-nitro-5-(1-pyrrolidinyl)-6-chlorobenzaldehyde,
2-nitro-5-(1-piperidinyl)-6-chlorobenzaldehyde,
2-nitro-5-dimethylamino-4-chlorobenzaldehyde,
2-nitro-5-(1-piperidinyl)-4-chlorobenzaldehyde,
2-nitro-5-(1-morpholinyl)-4-chlorobenzaldehyde,
2-nitro-5-(1-piperidinyl)-4-methylbenzaldehyde,
2-nitro-4-dimethylamino-6-chlorobenzaldehyde,
2-nitro-4-(1-piperidinyl)-6-chlorobenzaldehyde,
2-nitro-4-(1-piperidinyl)-5-methylbenzaldehyde,
2-nitro-4-(1-piperidinyl)-5-methoxybenzaldehyde,
2-nitro-5-(4-phenyl-1-piperazinyl)-6-chlorobenzaldehyde.

As stated above, the Formula I compounds or pharmaceutically acceptable salts thereof have pharmacological properties which make them particularly useful as phosphodiesterase inhibitors, blood platelet antiaggregators and/or cardiotonic agents. Regarding the latter, compounds of the invention selectively strengthen myocardial contraction force by which the heart ventricles pump blood into the periphery. Thus, the instant compounds are useful in the curative or prophylactic treatment of cardiac conditions such as myocardial failure where an increase in positive inotropic activity is desirable. Preferred compounds increase contractile force without unduly increasing heart rate.

Platelet aggregation is considered part of a complex physiological mechanism for formation of a thrombus in the vascular system. Thromboembolic phenomena, i.e., the formation of thrombi, are involved in hemostasis and a number of diseased states in mammals including thrombophlebitis, phlebothrombosis, cerebral thrombosis, coronary thrombosis and retinal vessel thrombosis. An increase in propensity for platelet aggregation, sometimes referred to as platelet adhesiveness, is observed following parturition, surgical operations such as coronary artery bypass surgery, organ transplant, angioplasty, prosthetic heart valve implants to name a few; and in ischaemic heart desease, atherosclerosis, multiple sclerosis, intracranial tumors, thromboembolism, and hyperlipemia; refer to A. Poplawski, et al., *J. Atherosclerosis Research*, 8, 721 (1968). Thus, the compounds of the invention which have antithrombogenic (inhibit blood platelet aggregation) and phosphodiesterase inhibition properties are useful in prevention or treatment of conditions involving platelet aggregation and thrombosis such as the above. Literature relating to prophylactic and therapeutic activities of phosphodiesterase inhibiting compounds include the following: S. M. Amer, "Cyclic Nucleotides as Targets For Drug Design," *Advances in Drug Research*, Vol. 12, 1977, Academic Press, London, pp 1–38; I. Weinryh, et al., *J. Pharm. Sci.*, pp 1556–1567 (1972); S. M. Amer, et al., *J. Pharm. Sci., Vol.* 64, pp 1–37 (1975); and D. N. Harris, et al., *Enzyme Inhibitors As Drugs*, McMillan & Co., Ed—M. Standler, pp 127–146, (1980). The instant compounds are considered to have antimetastatic potential in view of their platelet inhibition properties.

The pharmacological properties of the instant compounds can be demonstrated by conventional in vitro and in vivo biological tests such as the following.

In Vitro Inhibition of Platelet Aggregation

The aggregometer method of Born (1), as modified by Mustard, et al. (2) was used to assess the in vitro activity of the various compounds as to inhibition of adenosine diphosphate (ADP) and collagen-induced platelet aggregation. Platelet rich plasma (PRP) was separated by centrifugation from citrated (3.8 percent) rabbit blood. ADP in final concentration of 0.5 mcg/ml or 0.05 ml of a collagen suspension prepared according to the method described by Evans, et al. (3) was used to induce aggregation. The various compounds tested were dissovled in dimethylsulfoxide (DMSO) so that 5 mcl added to the platelet rich plasma would yield the desired test concentration. Vehicle control trials were done and compared with aggregation induced in platelet rich plasma containing various concentrations of the test compounds. Dose response curves were obtained and Effective Concentration (EC50) values calculated. In this test, the EC$_{50}$ values for dipyridamole, a clinically useful antithrombogenic agent, are >512 mcg/ml vs. ADP and 245 mcg/ml vs. collagen. Results are given in Table I hereinafter for various Formula I compounds.

1. Born, G. V. R., J. Physiol., London, 162, 67P (1962).
2. Mustard, J. F., Hegardt, B. Rowsell, H. C. and MacMillan, R. L., J. Lab. Clin. Med., 64, 548 (1964).
3. Evans, G., Marian M. C., Packham, M. A., Nishizawa, E. E., Mustard, J. F. and Murphy, E. A., J. Exp. Med., 128, 877 (1968).

Inhibition of Platelet Aggregation Following Oral Administration

This test is sometimes referred to in the art as an Ex vivo method and was initially described by Fleming, et al., *Arch. Int. Pharmacodyn. Ther.*, 199, 164 (1972). Briefly, the assay is essentially carried out as follows.

Aggregometry is performed in vitro as previously described on platelet rich plasma samples obtained from rats dosed with either test compounds or the vehicle. In all cases, activity is determined 2 hours after the drug is administered orally at various doses by gavage as a suspension in 0.9% water plus a few drops of Tween 20. Drug activity is expressed as $ED_{50}$'s (that dose required to inhibit the induced aggregation by 50%) calculated from results obtained from groups of 10 animals treated with various doses of test compounds in comparison to separate control groups.

In this test, the $ED_{50}$ of dipyridamole is greater than 100 mg/kg and anagrelide is 4.9 mg/kg. Results are given in Table I hereinafter for various Formula I compounds.

Inhibition of Cyclic AMP Phosphodiesterase

This assay is carried out essentially as described by Thompson, et al., *Methods in Enzymology*, 38, 205-212 (1974). Briefly, tritium labeled cyclic adenosine monophosphate (cAMP) is incubated with a phosphodiesterase (PDE) enzynme obtained from human platelets which converts a portion of the cAMP to 5'AMP in culture tubes. This reaction is terminated by submerging the tubes in a boiling water bath after which they are placed on ice and an aliquot of snake venom is added to each tube. This, during a second incubation, converts the 5'AMP to adenosine. Ion exchange resin is added to bind the remaining cyclic AMP. The tubes are centrifuged to sediment the resin and a portion of the clear supernatent (which contains radioactive adenosine) is counted in a liquid scintillation counter. The cAMP phosphodiesterase inhibition activity of a test agent is determined by pre-incubating the PDE enzyme preparation with the test agent. Dose response values are obtained and activity of the test agent reported as the molar (M) concentration of the test agent inhibiting 50% of the PDE activity ($IC_{50}$s). In this test, the $IC_{50}$ value of milrinone, a known inotropic agent, is $2 \times 10^{-7}$ molar. Results are given in Table I hereinafter for various Formula I compounds.

In Vivo Inotropic Activity

This test is carried out in ferrets as follows.

Fasted anesthetized ferrets are instrumented to study hemodynamic parameters as well as right ventricular contractile force (RVCF) using a Walton-Brodie open strain guage arch. Drugs are administered intraduodenally as solutions in DMSO (1 mL or less) and effects on myocardial contractile force and other parameters are monitored for 60 minutes after dosing. Changes in contractile force in response to drug treatment are expressed in terms of percent change from predose control.

In this test, milrinone produces a 52% increase in RVCF at 3 mg/kg. Results are given in Table II hereinafter for several Formula I compounds.

TABLE I

Inhibition of Platelet Aggregation and cAMP Phosphodiesterase

| Example[a] | Platelet Inhibition In Vitro - Rabbit PRP $EC_{50}$ (mcg/ml) vs. ADP | Platelet Inhibition In Vitro - Rabbit PRP $EC_{50}$ (mcg/ml) vs. collagen | Ex Vivo vs. ADP $ED_{50}$ (mg/kg) | cAMP Phosphodiesterase Human Platelets $IC_{50}$ (M) |
|---|---|---|---|---|
| 4 | 2.0 | 0.8 | | $7 \times 10^{-7}$ |
| 5 | 0.6 | 0.4 | >10 | $1 \times 10^{-6}$ |
| 6 | 0.15 | 0.09 | 5.6 | $2 \times 10^{-7}$ |
| 7 | 1.0 | 0.3 | 20 | $3 \times 10^{-8}$ |
| 8 | 0.6 | 0.4 | | $5 \times 10^{-8}$ |
| 9 | 0.3 | 0.2 | | $7 \times 10^{-8}$ |
| 10 | 0.03 | 0.02 | 12.2 | $2 \times 10^{-8}$ |
| 11 | 0.04 | 0.012 | | $3 \times 10^{-7}$ |
| 12 | 3.5 | 3.0 | | $2 \times 10^{-8}$ |
| 13 | 0.8 | 0.17 | | $7 \times 10^{-7}$ |
| 14 | 0.125 | 0.06 | | $6 \times 10^{-7}$ |
| 15 | 3 | 2 | | $3 \times 10^{-7}$ |
| 16 | 0.12 | 0.025 | | $5 \times 10^{-6}$ |
| 17 | 1.5 | 0.75 | | $3 \times 10^{-6}$ |

[a]Refer to examples below for compound identification.

TABLE II

Ferret In Vivo Inotropic Activity Maximum Percentage Change Following Intraduodenal Administration

| Example[a] | Dose (mg/kg) | Right Ventricular Contractile Force | Blood Pressure | Number of Animals |
|---|---|---|---|---|
| 6 | 3 | 9 ± 4 | −8 ± 6 | 3 |
| 7 | 3 | 22 ± 8 | −39 ± 3 | 3 |
| 7 | 0.3 | 14 ± 12 | −21 ± 5 | 3 |

[a]Refer to examples below for compound identification.

As stated above, one aspect of this invention relates to a therapeutic method for inhibiting phosphodiesterase and blood platelet aggregation in a mammal which comprises administering a therapeutically effective amount of a compound of Formula I or a pharmaceutically acceptable salt thereof to a mammal ia need of such treatment. Another aspect of this invention as stated above relates to a therapeutic method for increasing heart inotropic activity which comprises administering to a warm-blooded animal, including man, in need of such treatment a therapeutically effective amount of a compound of Formula I.

The dosage employed in the instant therapeutic methods will vary with the form of administration, the particular compound chosen, the subject being tested and the effect desired. Suitable effective dose in animals range from 0.5-30 mg/kg body weight orally and from 0.05-10 mg/kg body weight parenterally (generally characterized as subcutaneous, intramuscular, and intravenous injection). In accordance with conventional clinical practice, the effective dose in man can be determined by administering a Formula I compound at a dosage substantially less then the dose of the compound which is thought to be effective and then increasing the dosage in small increments until the desired effect is achieved.

In carrying out the instant therapeutic methods, the active ingredient of Formula I and pharmaeutically acceptable acid addition salts thereof are preferably administered with a pharmaceutically acceptable carrier and such compositions constitute part of the instant invention. Suitable dosage forms for oral use are tablets, dispersible powders, granules, capsules, syrups and elixirs. Examples of parenteral forms are solutions, suspensions, dispersions, emulsions, and the like. The compositions for oral use may contain one or more conventional adjuvants, such as sweetening agents, flavoring agents, coloring agents and preserving agents, in order to provide a composition of suitable pharmaceutical elegance. Tablets may contain the active ingredient in admixture with conventional pharmceutical acceptable excipients including inert diluents such as calcium carbonate, sodium carbonate, lactose and talc; granulating and disintegrating agents such as starch and alginic acid; binding agents such as starch, gelatin and acacia and lubricating agents such as magnesium stearate, stearic acid and talc. The tablets may be uncoated or coated by known techniques to delay disintegration and absorption in the gastrointestinal tract and thereby provide a sustained action over a longer period. Similarly, suspension, syrups and elixirs may contain the active ingredient in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl-p-hydroxybenzoate. Capsules may contain the active ingredient alone or admixed with an inert solid diluent such as calcium carbonate, calcium phosphate and kaolin. The injectible compositions are formulated as known in the art and may contain appropriate dispersing or wetting agents and suspending agents identical or similar to those mentioned above.

The following examples are given by way of illustration and are not to be construed as limiting the invention in any way inasmuch as many variations of the invention are possible within the spirit of the invention. All temperatures are degrees centrigrade and melting points taken with a Thomas Hoover capillary apparatus are uncorrected. Conventional abbreviations are employed in reporting Nuclear Magnetic Resonance (NMR) spectral data with tetramethylsilane as internal reference and chemical shift data values in parts per million.

EXAMPLE 1

METHOD A—Preparation of Hydantoin Intermediate of Formula II by Condensation of 2-Nitrobenzaldehyde (III) with Hydantoins (IV) by Adaptation of the Method of Billek, *Montash Chem.*, 92, 352–360 (1961)

(1-1)

N-[3-[(2,4-Dioxoimidazolidin-5-ylidene)methyl]-4-nitrophenyl]acetamide

A mixture of N-(3-formyl-4-nitrophenyl)acetamide (7.18 g, 35 mmol), hydantoin (3.65 g, 35 mmol), fused sodium acetate (2.83 g, 35 mmol) and acetic anhydride (70 mL) was heated at reflux for 1.5 hours. The mixture was cooled, diluted with water 250 mL (added in 50 mL aliquots over 40 minutes) and extracted with dichloromethane. The combined extracts were washed with water, dried over magnesium sulfate and the solvent evaporated. The residual oil was dissolved in methanol (100 mL) and 4N sodium hydroxide solution (100 mL) added. The mixture was stirred for 30 minutes at room temperature before adding 5N hydrochloric acid solution (80 mL) to precipitate a brown solid which was collected, washed with water and dried in air to give N-3-[(2,4-dioxoimidazolidin-5-ylidene)methyl]-4-nitrophenyl]acetamide (5.2 g, 52%), m.p. 297°–298° C. (dec.).

NMR (DMSO-$d_6$): delta 2.14 (3H, s, NH.CO.CH$_3$), 6.70 and 6.74 (1H, s, olefinic $\underline{H}$, ratio 1:7), 7.75 (1$\underline{H}$, d, J=2 Hz, aromatic $\underline{H}$ ortho to NAc), 7.90 (1H, dd, J=9 Hz, J'=2 Hz, aromatic $\underline{H}$ ortho to NAc) and 8.15 (1H, d, J=9 Hz, aromatic $\underline{H}$ ortho to NO$_2$).

(1-2)

5-[[(2-Nitro-5-(1-piperidinyl)phenyl]methylene]-2,4-imidazolidinedione

A mixture of 2-nitro-5-(1-piperidinyl)benzldehyde (1.0 g, 4.3 mmol), hydantoin (0.43 g, 4.3 mmol), fused sodium acetate (0.35 g, 4.3 mmol) and acetic anhydride (10 mL) was heated at reflux under an atmosphere of nitrogen. After 1 hour, the mixture was cooled and diluted with water (20 mL) added portionwise. The mixture was extracted with dichloromethane, the combined extracts washed with water and concentrated in vacuo. The residue was dissolved in methanol (10 mL) and 4N sodium hydroxide solution (11 mL) added. After 1 hour, additional 4N NaOH was added until basic, the mixture stirred for 1 hour and then 3N hydrochloric acid solution added until pH=7. The solid was filtered off, washed with water and dried in air. Crystallization from aqueous dimethylformamide afforded 5-[[2-nitro-5-(1-piperidinyl)phenyl]methylene]2,4-imidazolidinedione (0.34 g, 25%), m.p. 284° C. (dec.).

Anal. Calcd. for $C_{15}H_{16}N_4O_4$: C, 56.96; H, 5.10; N, 17.71. Found: C, 56.65; H, 5.08; N, 17.33.

NMR (DMSO-$d_6$): delta 1.62 (6H, bs, $\underline{CH_2}$ of piperidine ring), 3.49 (4H, bs, N$\underline{CH_2}$), 6.78 (1H, s, olefinic H), 6.85 (1H, d, J=2 Hz, aromatic H meta to NO$_2$), 6.96 (1H, dd, J=9 Hz, J'=2 Hz, aromatic $\underline{H}$ meta to NO$_2$), and 8.05 (1H, d, J=9 Hz, aromatic $\underline{H}$ ortho to NO$_2$).

EXAMPLE 2

METHOD B—Preparation of Hydantoin Intermediate of Formula II by Condensation of 2-Nitrobenzaldehyde (III) with Hydantoin-5-phosphonate (VI)

(2-1)

5-[[2-Nitro-5-(1-piperidinyl)phenyl]methylene]-2,4-imidazolidinedione

Sodium (0.6 g, 0.026 g atom) was dissolved in absolute ethanol (200 mL) and diethyl 2,4-dioxoimidazolidine-5-phosphonate (6.0 g, 25 mmol) added. After 10 minutes, 2-nitro-5-(1-piperidinyl)benzaldehyde (5.0 g, 21 mmol) was added in one portion and the mixture stirred at room temperature for 5 hours. The yellow precipitate was filtered off, washed with water and dried in air to give 5-[[2-nitro-5-(1-piperidinyl)phenyl]-methylene]-2,4-imidazolidinedione (6.17 g, 92%), m.p. 273°–276° C. A sample dried in vacuo in 110° C. had m.p. 280° C. (dec.).

Anal. Calcd. for $C_{15}H_{16}N_4O_4$: C, 56.96; H, 5.10; N, 17.71. Found: C, 56.64; H, 5.06; N, 17.51.

NMR (DMSO-$d_6$): delta 1.62 (6H, bs, $\underline{CH_2}$ of piperidine ring), 3.49 (4H, bs, N$\underline{CH_2}$), 6.67 and 6.78 (1H, 2 singlets, ratio 3:1, olefinic $\underline{H}$), 6.80 to 7.00 (2H, m, aromatic $\underline{H}$ ortho to piperidino group) and 7.90 to 8.10 (1H, two doublets, J=9 Hz, aromatic $\underline{H}$ ortho to NO$_2$).

(2-2)

5-[[2-Nitro-5-(1-pyrrolidinyl)phenyl]methylene]-2,4-imidazolidinedione

Prepared from diethyl 2,4-dioxoimidazolidine-5-phosphonate and 2-nitro-5-(1-pyrrolidinyl)benzaldehyde analogous to the procedure of Example (2-1), m.p. 289° C. (dec.), crystallized from DMF-H$_2$O.

Anal. Calcd. for $C_{14}H_{14}N_4O_4$: C, 55.63; H, 4.67; N, 18.53. Found: C, 55.73; H, 4.66; N, 18.51.

(2-3)

5-[[5-(Diethylamino)-2-nitrophenyl]methylene]-2,4-imidazolidinedione

Prepared as a partial hydrate from diethyl 2,4-dioxoimidazolidine-5-phosphonate and 2-nitro-5-diethylaminobenzaldehyde analogous to the procedure of Example (2-1), m.p. 251°-252° C. (dec.), crystallized from EtOH-H$_2$O.

Anal. Calcd. for C$_{14}$H$_{16}$N$_4$O$_4$.0.2H$_2$O: C, 54.61; H, 5.37; N, 18.20; H$_2$O, 1.17. Found: C, 54.62; H, 5.21; N, 17.92; H$_2$O; 3.72*.

(*Karl Fischer reagent reacted with compound and produced erroneous results.)

(2-4)
5-[[5-(4-Morpholinyl)-2-nitrophenyl]methylene]-2,4-imidazolidinedione

Prepared as a partial solvate/hydrate from diethyl 2,4-dioxoimidazolidine-5-phosphonate and 2-nitro-5-(4morpholinyl)benzaldehyde analogous to the procedure of Example (2-1), m.p. 278°-280° C., crystallized from EtOH-H$_2$O.

Anal. Calcd. for C$_{14}$H$_{14}$N$_4$O$_5$0.2C$_2$H$_6$O0.25H$_2$O: C, 52.10; H, 4.77; N, 16.88; H$_2$O, 1.36. Found: C, 51.74; H, 4.67; N, 16.64; H$_2$O, 0.99.

(2-5) Ethyl 1-[3-[(2,4-dioxoimidazolidin-5-ylidene)methyl]-4-nitrophenyl]-4-piperidinecarboxylate Prepared from diethyl 2,4-dioxoimidazolidine-5-phosphonate and 2-nitro-5-(4-ethoxycarbonyl-1-piperidinyl)benzaldehyde analogous to the procedure of Example (2-1), m.p. 221°-223° C., crystallized from MeOH.

Anal. Calcd. for C$_{18}$H$_{20}$N$_4$O$_6$: C, 55.67; H, 5.19; N, 14.43. Found, 55.62; H, 5.28; N, 14.40.

(2-6) Ethyl 4-[3-[(2,4-dioxoimidazolidin-5-ylidene)methyl]-4-nitrophenyl]-1-piperazinecarboxylate Prepared as a partial hydrate from diethyl 2,4-dioxoimidazolidine-5-phosphonate and 2-nitro-5-[4-(ethoxycarbonyl)-1-piperazinyl)]benzaldehyde analogous to the procedure of Example (2-1), m.p. 274°-275° C., crystallized from EtOH-H$_2$O.

Anal. Calcd. for C$_{17}$H$_{19}$N$_5$O$_6$0.25H$_2$O: C, 51.84; H, 4.99; N, 17.78; H$_2$O, 1.14. Found: C, 51.94; H, 5.04; N, 17.41; H$_2$O, 1.33.

(2-7)
1-Benzoyl-4-[3-[(2,4-dioxoimidazolidin-5-ylidene)methyl]-4-nitrophenyl]piperazine Prepared as a partial hydrate from diethyl 2,4-dioxoimidazolidine-5-phosphonate and 2-nitro-5-(4-benzoyl-1-piperazinyl)benzaldehyde analogous to the procedure of Example (2-1), m.p. 165°-170° C., crystallized from DMF-H$_2$O.

Anal. Calcd. for C$_{21}$H$_{19}$N$_4$O$_5$0.5H$_2$O: C, 58.60; H, 4.68; N, 16.27; H$_2$O, 2.09. Found: C, 58.86; H, 4.98; N, 16.32; H$_2$O, 2.35.

(2-8)
1-(3,4-Dimethoxybenzoyl)-4-[(2,4-dioxoimidazolidin-5-ylidene)methyl]-4-nitrophenyl]piperazine Prepared as a partial hydrate from diethyl 2,4-dioxoimidazoldine-5-phosphonate and 2-nitro-5-[4-(3,4-dimethoxybenzoyl)-1-piperazinyl]benzaldehyde analogous to the procedure of Example (2-1), m.p. 200°-203° C., crystallized from CH$_3$CN.

Anal. Calcd. for C$_{23}$H$_{23}$N$_5$O$_7$0.12H$_2$O: C, 57.38; H, 4.82; N, 14.55; H$_2$O, 0.45. Found: C, 57.03; H, 4.77; N, 14.49; H$_2$O, 0.44.

(2-9) Ethyl 1-[3-[(2,4-dioxoimidazolidin-5-ylidene)methyl]-4-nitrophenyl]-3-piperidinecarboxylate Prepared from diethyl 2,4-dioxoimidazolidine-5-phosphonate and 2-nitro-5-[3-(ethoxycarbonyl)-1-piperidinyl)]benzaldehyde analogous to the procedure of Example (2-1), m.p. 223°-225° C.

Anal. Calcd. for C$_{18}$H$_{20}$N$_4$O$_6$: C, 55.67; H, 5.19; N, 14.43. Found: C, 55.50; H, 5.22; N, 14.26.

(2-10)
N-Cyclohexyl-1-[3-[(2,4-dioxoimidazolidin-5-ylidene)-methyl]-4-nitrophenyl]-N-methyl-4-piperidinecarboxamide Prepared as a partial hydrate from diethyl 2,4-dioxoimidazolidine-5-phosphonate and 2-nitro-5-[4-(N-methyl-N-cyclohexylcarbamoyl)-1-piperidinyl]benzaldehyde analogous to the procedure of Example (2-1), indistinct m.p. 162°-170° C., crystallized from MeOH-H$_2$O.

Anal. Calcd. for C$_{23}$H$_{29}$N$_4$O$_5$0.25H$_2$O: C, 60.05; H, 6.46; N, 15.22; H$_2$O, 0.98. Found: C, 60.21; H, 6.41; N, 15.15; H$_2$O, 1.07.

(2-11)
N-Cyclohexyl-1-[3-[(2,4-dioxoimidazolidin-5-ylidene)-methyl]-4-nitrophenyl]-N-methyl-3-piperidinecarboxamide Prepared from diethyl 2,4-dioxoimidazolidine-5-phosphonate and 2-nitro-5-[3-(N-methyl-N-cyclohexylcarbamoyl)-1-piperidinyl]benzaldehyde analogous to the procedure of Example (2-1), m.p. 153°-162° C., crystallized from MeOH-H$_2$O.

Anal. Calcd. for C$_{23}$H$_{29}$N$_5$O$_5$: C, 60.65; H, 6.42; N, 15.37. Found: C, 60.62; H, 6.55; N, 14.97.

(2-12)
1-[3-[(2,4-dioxoimidazolidin-5-ylidene)methyl]-4-nitrophenyl]-4-phenylpiperazine Prepared from diethyl 2,4-dioxoimidazolidine-5-phosphonate and 2-nitro-5-[4-(phenyl)-1-piperazine]-benzaldehyde analogous to the procedure of Example (2-1), m.p. 230°-236° C. (dec.), crystallized from EtOH.

(2-13) By substituting the benzaldehydes:
2-nitro-5-dimethylamino-6-chlorobenzaldehyde,
2-nitro-5-diethylamino-6-chlorobenzaldehyde,
2-nitro-5-(1-pyrrolidinyl)-6-chlorobenzaldehyde,
2-nitro-5-(1-piperidinyl)-6-chlorobenzaldehyde,
2-nitro-5-dimethylamino-4-chlorobenzaldehyde,
2-nitro-5-(1-piperidinyl)-4-chlorobenzaldehyde,
2-nitro-5-(1-morpholinyl)-4-chlorobenzaldehyde,
2-nitro-5-(1-piperidinyl)-4-methylbenzaldehyde,
2-nitro-4-dimethylamino-6-chlorobenzaldehyde,
2-nitro-4-(1-piperidinyl)-6-chlorobenzaldehyde,
2-nitro-4-(1-piperidinyl)-5-methylbenzaldehyde,
2-nitro-4-(1-piperidinyl)-5-methoxybenzaldehyde,
2-nitro-5-(4-phenyl-1-piperazinyl)-6-chlorobenzaldehyde for 2-nitro-5-(1-piperidinyl)benzaldehyde in the procedure of Example (2-1), the following hydantoin intermediates of Formula II wherein R$_1$ is hydrogen are prepared.

(II)

[Structure of formula (II): benzene ring with R2 at position 4, NO2 at position 3-adjacent, R3R4N- at position 5, connected via CH=C to an imidazolidine-2,4-dione (hydantoin) ring with N-R1]

|     | R₂    | NR₃R₄                    |
|-----|-------|--------------------------|
| (a) | 6-Cl  | 5-dimethylamino          |
| (b) | 6-Cl  | 5-diethylamino           |
| (c) | 6-Cl  | 5-(1-pyrrolidinyl)       |
| (d) | 4-Cl  | 5-(1-piperidinyl)        |
| (e) | 4-Cl  | 5-dimethylamino          |
| (f) | 4-Cl  | 5-(1-piperidinyl)        |
| (g) | 4-Cl  | 5-(1-morpholinyl)        |
| (h) | 4-Me  | 5-(1-piperidinyl)        |
| (i) | 6-Cl  | 4-dimethylamino          |
| (j) | 5-Me  | 4-(1-piperidinyl)        |
| (k) | 5-MeO | 4-(1-piperidinyl)        |
| (l) | 6-Cl  | 5-(4-phenyl-1-piperazinyl) |

The corresponding hydantoins wherein $R_1$ is methyl are obtained by using the appropriate benzaldehyde and diethyl 1-methyl-2,4-dioxoimidazolidine-5-phosphonate.

EXAMPLE 3

Preparation of Benzaldehyde Intermediates of Formula (III)

(3-1) Preparation of 2-nitro-5-(1-piperidinyl)benzaldehyde according to Scheme 1

Step (a) 5-Chloro-2-nitrobenzenemethanol: A solution of borane:tetrahydrofuran complex (25.8 g, 0.3 mole) in tetrahydrofuran (THF) (300 mL) was added dropwise to a stirred solution of 5-chloro-2-nitrobenzoic acid (50.0 g, 0.24 mole) in dry THF (400 mL) maintained at 0° C. under an atmosphere of nitrogen. After completion of the addition, the mixture was heated at 50° C. for 96 hours before being cooled in an ice bath. Hydrochloric acid (10% solution) was added dropwise and the mixture refluxed for 30 minutes. The THF was removed in vacuo and the residue extracted with dichloromethane (3×350 mL). Combined extracts were washed with saturated sodium bicarbonate solution, dried over magnesium sulfate and the solvent evaporated to give a solid (45 g, 100%), crystallization from chloroform-hexane gave 5-chloro-2-nitro-benzenemethanol (41.0 g, 91%) mp 79°–81° C.

Anal. calcd. for $C_7H_6ClNO_3$: C, 44.82; H, 3.22; N, 7.47. Found: C, 44.74; H, 3.19; N, 7.51.

Step (b) 5-Chloro-2-nitrobenzaldehyde: A solution of 5-chloro-2-nitrobenzenemethanol (20 g, 0.11 mole) in dry dichloromethane (150 mL) was added in one portion to a vigorously stirred solution of pyridinium chlorochromate (43.2 g, 0.2 mole) in dry dichloromethane (200 mL). The reaction mixture was stirred at room temperature overnight, diluted with diethyl ether (about 1300 mL) and the organic phase decanted onto a plug of silica gel (6″ deep). Elution with diethyl ether and removal of the solvent left a light yellow solid, 5-chloro-2-nitrobenzaldehye (17.7 g, 89%) mp 76°–77° C.

This intermediate and analogous ortho-nitrobenzaldehyde can also be obtained by nitrating the benzaldehyde as described by E. J. Alford, et al; Chem. Soc., 2105 (1952).

Step (c) 2-(5-Chloro-2-nitrophenyl)-1,3-dioxolane: Prepared as described by D. E. O'Brien et al, *J. Het. Chem.*, 7, 102 (1970) as follows. A mixture of 5-chloro-2-nitrobenzaldehyde (18.3 g, 0.1 mole), ethylene glycol (7.0 g, 0.11 mole) p-toluenesulfonic acid (0.5 g) and benzene (850 mL) was stirred and refluxed with continuous removal of water via a Dean and Stark trap for 24 hours. The solvent was removed, the residue dissolved in dichloromethane and filtered through a plug of silica gel (6″ deep). Evaporation of the solvent afforded 2-(5-chloro-2-nitrophenyl)-1,3-dioxolane (21.8 g, 97%) as an oil.

Anal. calcd. for $C_9H_8ClNO_4$: C, 47.08; H, 3.51; N, 6.10. Found: C, 47.21; H, 3.60; N, 5.98.

Step (d) 2-(2-Nitro-5-piperdinylphenyl)-1,3-dioxolane: A mixture of 2-(5-chloro-2-nitrophenyl)-1,3-dioxolane (21.3 g, 0.09 mole) and piperidine (39.6 g, 0.46 mole) was heated at reflux in an oil bath. After 3 hours, excess piperidine was evaporated and the residue partitioned between water and dichloromethane. The organic phase was separated and the aqueous layer extracted with dichloromethane. Combined extracts were washed with water, dried over magnesium sulfate and concentrated in vacuo to afford 2-(2-nitro-5-piperdinylphenyl)-1,3-dioxolane (21.6 g, 100%) as a dark colored oil which was used without further purification. An analytical sample was purified by flash chromatography using dichloromethane as eluant to give a light yellow oil.

Anal. calcd. for $C_{14}H_{18}N_2O_4$: C, 60.42; H, 6.52; N, 10.07. Found: C, 60.24; H, 6.62; N, 9.90.

Step (e) 2-Nitro-5-(1-piperidinyl)benzaldehyde: A mixture of 2-(2-nitro-5-piperidinylphenyl)-1,3-dioxolane (26.1 g, 0.09 mole), tetrahydrofuran (THF) (1 L), water (315 mL) and 3N hydrochloric acid solution (130 mL) was heated at reflux for 45 minutes. The mixture was cooled to room temperature and the THF evaporated. The residue was cooled in an ice bath, the precipitate filtered, washed with water and dried in air to give 2-nitro-5-(1-piperindyl)benzaldehyde (19.2 g, 87%) mp 100°–102° C., which was used without further purification. An analytical sample was purified by chromatography on silica gel using dichloromethane as eluant followed by crystallization from acetonitrile and had mp 102°–103° C.

Anal. calcd. for $C_{12}H_{14}N_2O_3$: C, 61.53; H, 6.02; N, 11.96. Found: C, 61.49; H, 6.01; N, 12.04.

(3-2) Preparation of 1-(3,4-dimethoxybenzoyl)-4-(3-formyl-4-introphenyl)-piperazine according to Scheme 2

Step (a) 2-(2-Nitro-5-piperazinylphenyl)-1,3-dioxolane: A mixture of 2-(5-chloro-2-nitrophenyl)-1,3-dioxolane (7.0 g, 38 mmol) and piperazine (8.2 g, 95 mmol) was heated in an oil bath at 120°–130° C. for 90 minutes. The mixture was diluted with water and 10% sodium carbonate solution and extracted with dichloromethane. Combined extracts were washed with dilute sodium carbonate solution and water, dried over magnesium sulfate and concentrated to give a gum (8.3 g) which was dissolved in dichloromethane. Hydrogen chloride (10% in methanol) was added until acidic, the precipitate filtered off, washed with dichloromethane and dried in air to give 2-(2-nitro-5-piperazinylphenyl)-1,3-dioxolane as the hydrochloride salt (7.4 g, 62%) mp 178°–180° C. (dec).

Anal. calcd. for $C_{13}H_{17}N_3O_4$: C, 55.91; H, 6.14; N, 15.04. Found: C, 56.51; H, 5.99; N, 16.54.

Step (b) 2-[2-Nitro-5-[4-(3,4-dimethoxybenzoyl)-piperazinyl]phenyl]-1,3-dioxolane. 2-(2-Nitro-5-piperazinylphenyl)-1,3-dioxolane (6.63 g, 24 mmol) was added portionwise over 1 hour to a stirred solution of 3,4-dimethoxybenzoyl chloride (4.76 g, 24 mmol) and pyridine (4.04 g, 48 mmol) in dry dichloromethane (200 mL). The mixture was stirred overnight at room temperature, washed twice with water and concentrated in vacuo to provide 2-[2-nitro-5-[4-(3,4-dimethoxybenzoyl)piperazinyl]phenyl]-1,3-dioxolane used without further purification below.

Step (d) 1-3,4-Dimethoxybenzoyl)-4-(3-formyl-4-nitrophenyl)piperazine: The step (b) dioxolane intermediate was combined with tetrahydrofuran (265 mL, water (80 mL) and 3N hydrochloric acid (33 mL) solution and the mixture refluxed. After 2 hours, the THF was removed in vacuo, the residue diluted with water and dichloromethane and filtered to afford a first crop of solid (3.26 g). The organic phase was separated, washed with 10% sodium carbonate solution and water, dried over magnesium sulfate and concentrated in vacuo to afford a solid which was stirred in ethanol filtered and combined with the first crop to afford (7.36 g, 77%) of 1-(3,4-dimethoxybenzoyl)-4-(3-formyl-4-nitrophenyl)piperazine. An analytical sample was obtained by crystallization from chloroform/ethanol and had mp 200°-201° C.

Anal. calcd. for $C_{20}H_{21}N_3O_6$: C, 60.14; H, 5.30; N, 10.52. Found: C, 60.08; H, 5.38; N, 10.45.

(3-3) Preparation of N-(3-formyl-4-nitrophenyl)acetamide according to Scheme 3:

Step (a) 2-(3-Nitrophenyl)-1,3-dioxolane: A mixture of 3-nitrobenzaldehyde (100 g, 0.66 mole), ethylene glycol (49.3 g, 0.7 mole) and p-toluenesulfonic acid (0.8 g) and benzene (1 L) was heated at reflux with continuous removal of water via a Dean and Stark trap. After 4 hours, the mixture was cooled, filtered through a pad of neutral alumina and concentrated in vacuo to afford 2-(3-nitrophenyl)-1,3-dioxolane (130.4 g, 100%) as an amber oil used without further purification below.

Step (b) 2-(3-Aminophenyl)-1,3-dioxolane: A solution of 2-(3-nitrophenyl)-1,3-dioxolane (64.4 g, 0.33 mole) in ethyl acetate (1 L) was hydrogenated over 10% palladium on charcoal (3 g) at 50 p.s.i. After 2.5 hours, hydrogen uptake ceased, the reaction mixture containing 2-(3-aminophenyl)-1,3-dioxolane was filtered through kieselguhr and used below.

Step (c) N-[3-(1,3-Dioxolan-2-yl)phenyl]acetamide: Pyridine (31.3 g, 0.4 mole) was added to the above cooled (ice bath) ethylacetate solution of 2-(3-aminophenyl)1,3-dioxolane followed by dropwise addition of acetyl chloride (31.1 g, 0.4 mole) in ethyl acetate (50 mL) over 45 minutes. The ice bath was removed and the mixture stirred at room temperature for 30 minutes before being washed with water and dried over magnesium sulfate. Evaporation of the solvent afford N-[3-(1,3-dioxolan-2-yl)phneyl]acetamide (58.2 g, 85%) as an amber oil used without further purification below.

Step (d) N-(3-Formylphenyl)acetamide: A solution of N-[3-(1,3-dioxolan-2-yl)phenyl]acetamide (50.0 g, 0.24 mole) and p-toluenesulfonic acid (1.0 g) in acetone (750 mL) was stirred at room temperature for 72 hours. The solution was filtered through a pad of neutral alumina and concentrated in vacuo to afford N-(3-formylphenyl)acetamide (39.4 g, 100%), mp 68°-70° C., used without further purification below.

Step (e) N-(3-Formyl-4-nitrophenyl)acetamide: A solution of potassium nitrate (6.2 g, 61 mmol) in sulfuric acid (30 mL) was added dropwise to stirred solution of N-(3-formylphenyl)acetamide (10.0 g, 61 mmol) in sulfuric acid (120 mL) maintained at 5° C. After 2 hours, the reaction mixture was poured onto ice water (500 mL) and filtered to give N-(3-formyl-4-nitrophenyl)acetamide (6.2 g, 48%) mp 131°-135° C., used without further purification.

EXAMPLE 4

N-(2,3-Dihydro-2-oxo-1H-imidazo[4,5-b]quinolin-7-yl)acetamide

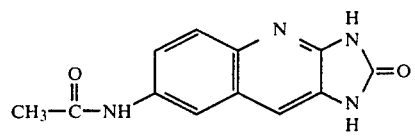

A solution of N-[3(2,4-dioxoimidazolidine-5-ylidene)-methyl]-4-nitrophenyl]acetamide (5.0 g, 17 mmol) in dimethylformamide (150 mL) was hydrogenated over 10% palladium on charcoal (0.95 g) at 50 p.s.i. in a low pressure hydrogenation apparatus. After 19 hours, the mixture was filtered through kieselguhr and the solvent evaporated. The residual solid was suspended in refluxing methanol (250 mL) and iodine (2.18 g, 9 mmol) added. After 40 minutes, the mixture was concentrated to about 100 mL and diluted with 10% sodium thiosulfate solution (100 mL) and 10% sodium carbonate solution (100 mL). The mixture was concentrated in vacuo and filtered to give N-(2,3-dihydro-2-oxo-1H-imidazo[4,5-b]quinolin-7-yl)acetamide (1.92 g, 46%) which crystallized from methanol afforded pure product as a partial hydrate (1.75 g, 42%), m.p. >320° C.

Anal. Calcd. for $C_{12}H_{10}N_4O_2 \cdot 0.3H_2O$: C, 58.20; H, 4.31; N, 22.62; $H_2O$, 2.18. Found: C, 58.12; H, 4.24; N, 22.27; $H_2O$, 1.60.

NMR (DMSO-$d_6$): delta 1.98 (3H, s, N.CO.C$\underline{H}_3$), 7.20 to 7.60 (3H, m, aromatic $\underline{H}$) and 7.94 (1H, s, aromatic $\underline{H}$ ortho to NH.CO).

EXAMPLE 5

7-Amino-1,3-dihydro-2H-imidazo[4,5-b]quinolin-2-one

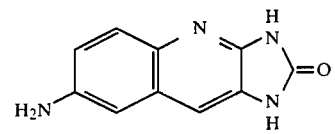

A suspension of N-(2,3-dihydro-2-oxo-1H-imidazo[4,5-b]quinolin-7-yl)acetamide (3.0 g, 12 mmol) in 6N hydrochloric acid solution (60 mL) was heated on a steam bath for 30 minutes to afford a solution. Evaporation of the solvent afforded the dihydrochloride salt of 7-amino-1,3-dihydro-2H-imidazo[4,5-b]quinolin-2-one as a partial hydrate (3.33 g, 96%), m.p. >300° C.

Anal. Calcd. for $C_{10}H_8N_4O \cdot 2HCl \cdot 0.3H_2O$: C, 43.12; H, 3.84; N, 20.11; $H_2O$, 1.94. Found: C, 43.30; H, 3.96; N, 19.62; $H_2O$, 1.91.

NMR (DMSO-$d_2$): delta 7.57 (1H, d, J=6 Hz, aromatic $\underline{H}$), 7.81 (1H, s, aromatic $\underline{H}$), 7.92 (2H, m, aromatic $\underline{H}$).

EXAMPLE 6

N-(2,3-Dihydro-2-oxo-1H-imidazo[4,5-b]quinolin-7-yl)benzamide

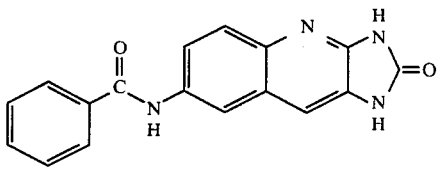

Benzoic anhydride (2.26 g, 10 mmol) was added to a stirred suspension of 7-amino-1,3-dihydro-2H-imidazo[4,5-b]quinolin-2-one (1.0 g, 5 mmol) in dimethylformamide (20 mL) and pyridine (0.4 mL). After 1.5 hours, additional benzoic anhydride (1.3 g, 5 mmol), pyridine (0.4 mL) and dimethylformamide (5 mL) were added. The mixture was stirred for 1.5 hours, diluted with water and filtered. The solid was washed with water, dried in vacuo, triturated with hot methanol and crystallized from methanol/dimethylformamide to give N-(2,3-dihydro-2-oxo-1H-imidazo[4,5-b]quinolin-7-yl)benzamide as a partial hydrate (1.5 g, 98%), m.p. >300° C.

Anal. Calcd. for $C_{17}H_{12}N_4O_2 \cdot 0.02H_2O$: C, 67.02; H, 3.98; N, 18.39; $H_2O$, 0.12. Found: C, 66.61; H, 4.12; N, 18.46; $H_2O$, 0.08.

NMR (DMSO-$d_6$): delta 7.55 to 8.15 (8H, m, aromatic $\underline{H}$) and 8.44 (1H, s, aromatic $\underline{H}$ ortho to NH.CO).

EXAMPLE 7

1,3-Dihydro-7-(1-piperidinyl)-2H-imidazo[4,5-b]quinolin-2-one

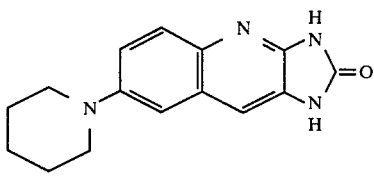

A solution of 5-[[2-nitro-5-(1-piperidinyl)phenyl]methylene]-2,4-imidazolidinedione (5.0 g, 15.8 mmol) in methanol (250 mL) and 5.7N HCl in ethanol (6 mL) was hydrogenated over 10% palladium on charcoal (0.8 g) at 50 p.s.i. in a low pressure hydrogenation apparatus. After 24 hours, the mixture was filtered through Kieselguhr, the solvent evaporated and the residue dissolved in methanol (100 mL). The mixture was heated to reflux and iodine (2.2 g, 8.7 mmol) added portionwise. Reflux was continued a further 30 minutes before concentrating to about 50 mL). 10% Sodium thiosulfate solution and 10% sodium carbonate solution was added, the mixture stirred for 1 hour and filtered. The solid was washed with water and methanol, dried in air and crystallized from a mixture of dimethylformamide, methanol and water to give a solid (2.2 g) which was refluxed in methanol to which excess 10% hydrogen chloride in ethanol was added. After solution occurred, the mixture was concentrated to about 30 mL and excess ethyl acetate added to precipitate the dihydrochloride salt of 1,3-dihydro-7-(1-piperidinyl)-2H-imidazo[4,5-b]quinolin-2-one as a partial hydrate (2.4 g, 44%), m.p. 300° C. (dec).

Anal. Calcd. for $C_{15}H_{16}N_4O \cdot 2HCl \cdot 0.6H_2O$: C, 51.18; H, 5.50; N, 15.91; $H_2O$, 3.07. Found: C, 50.93; H, 5.33; N, 15.72; $H_2O$, 2.70.

NMR (DMSO-$d_6$): delta 1.50 to 2.40 (6H, bs, $C\underline{H}_2$ of piperidine ring), 3.60 (4H, bs, $NC\underline{H}_2$), 7.00 (3H, bs, $N\underline{H}+H+$), 7.63 (1H, s, aromatic $\underline{H}$ ortho to NH.CO), 7.94 (1H, d, J=9 Hz), aromatic $\underline{H}$), 8.03 (1H, dd, J=9 Hz, J'=2 Hz, aromatic $\underline{H}$), 8.44 (1H, s, aromatic $\underline{H}$) and 11.31 (1H, s, $N\underline{H}$).

EXAMPLE 8

1,3-Dihydro-7-(1-pyrrolidinyl)-2H-imidazo-[4,5-b]quinolin-2-one

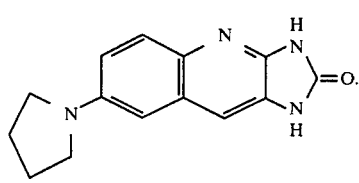

This compound, m.p. >300° C. (obtained as a dimethylformamide solvate by crystallization from methanol-dimethylformamide), was prepared analogous to Example 4 from 5-[[2-nitro-5-(1-pyrrolidinyl)phenyl]methylene]-2,4-imidazolidinedione.

Anal. Calcd. for $C_{14}H_{14}N_4O \cdot 0.15C_3H_7NO$: C, 65.43; H, 5.72; N, 21.92. Found: C, 65.06; H, 5.61; N, 21.81.

NMR (DMSO-$d_6$): delta 1.98 (4H, bs, $C\underline{H}_2$), 3.30 (4H, t, J=8 Hz, $NC\underline{H}_2$), 6.76 (1H, d, J=2 Hz, aromatic $\underline{H}$ ortho to N), 6.97 (1H, dd, J=9 Hz, J'=2 Hz, aromatic $\underline{H}$ ortho to N), 7.35 (1H, s, aromatic $\underline{H}$ ortho to NH.CO), and 7.60 (1H, d, J=9 Hz, aromatic $\underline{H}$ meta to N).

EXAMPLE 9

7-(Diethylamino)-1,3-dihydro-2H-imidazo[4,5-b]quinolin-2-one

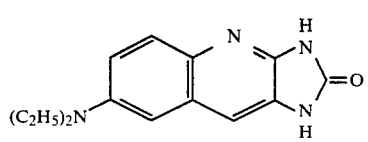

This compound, m.p. 300°-303° C. (dec) (obtained as a partial hydrate by crystallization from dimethylformamide water), was prepared analogous to Example 4 from 5-[[5-(diethylamino)-2-nitrophenyl]methylene]-2,4imidazolidinedione.

Anal. Calcd. for $C_{14}H_{16}N_4O \cdot 0.15H_2O$: C, 64.92; H, 6.34; N, 21.63; $H_2O$, 1.04. Found: C, 64.61; H, 6.15; N, 21.59; $H_2O$, 0.72.

NMR (DMSO-$d_6$): delta 1.12 (6H, t, J=7 Hz, $C\underline{H}_3$), 3.39 (4H, q, J=7 Hz, $NC\underline{H}_2$), 6.93 (1H, s, aromatic $\underline{H}$ ortho to N), 7.09 (1H, d, J=8 Hz, aromatic $\underline{H}$ ortho to N), 7.41 (1H, s, aromatic $\underline{H}$ ortho to NH.CO), 7.63 (1H, d, J=8 Hz, aromatic $\underline{H}$ meta to N), 10.86 (1H, bs, $N\underline{H}CO$) and 11.24 (1H, bs, $N\underline{H}.CO$).

EXAMPLE 10

1,3-Dihydro-7-(4-morpholinyl)-2H-imidazo[4,5-b]quinolin-2-one

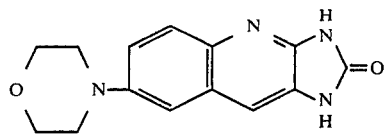

This compound, m.p. >310° C. (obtained as a partial hydrate hydrochloride salt by crystallization from methanol-ethyl acetate), was prepared analogous to Example 7 from 5-[[5-(4-morpholinyl)-2-nitrophenyl]methylene-2,4-imidazolidinedione.

Anal. Calcd. for $C_{14}H_{14}N_4O_2 \cdot HCl \cdot 0.7H_2O$: C, 52.65; H, 5.18; N, 17.54; $H_2O$, 3.95. Found: C, 52.93; H, 5.24; N, 17.41; $H_2O$, 4.20.

NMR (DMSO-$d_6$): delta 3.38 (4H, s, NC$\underline{H}_2$), 3.93 (4H, s, OC$\underline{H}_2$), 7.62 (1H, s, aromatic $\underline{H}$ ortho to NH.CO), 7.55 to 7.95 (5H, m, aromatic $\underline{H}$, NH.CO, $\underline{H}$+).

EXAMPLE 11

Methyl 1-(2,3-Dihydro-2-oxo-1H-imidazo[4,5-b]quinolin-7-yl)-4-piperidinecarboxylate

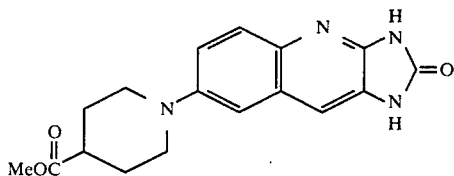

Ethyl 1-[3-[(2,4-dioxoimidazolidin-5-ylidene)methyl]-4-nitrophenyl]-4-piperidinecarboxylate (35.8 g, 92 mmol) in dimethylformamide (500 mL) was hydrogenated over 10% palladium on charcoal (3.6 g) at 200 psi pressure. After 42 hours, the mixture was filtered through kieselguhr, the solvent evaporated, and the residue diluted with 50% methanol/ether ether (500 mL). A light spray powder (25.0 g) was collected in two crops. The powder was added to methanol (500 mL) containing p-toluene sulfonic acid (1.5 g), and heated at reflux for 18 hours. Upon cooling, the mixture was filtered to give 19.5 g of an off white solid consisting of a mixture of ethyl 1-(1,3,9,9a-tetrahydro-2-oxo-1H-imidazo[4,5-b]quinolin-7-yl)-4-piperidinecarboxylate and the corresponding oxidized 2,3-dihydro compound (ethyl ester of the title compound). The solid was added to methanol (500 mL), heated to reflux, iodine (13.7 g, 54 mmol) added portionwise, and reflux continued for 2.5 hours. Upon cooling, 10% sodium thiosulfate and 10% sodium carbonate solution were added until pH=7. Water (300 mL) was added, and the precipitate consisting of the title compound collected (19.4 g, 65%).

An alternate preparation of the title compound involves hydrogenating ethyl 1-[3-[(2,4-dioxoimidazolidin-5-ylidene)methyl]-4-nitrophenyl]-4-piperidinecarboxylate (5.00 g, 13 mmol) in dimethylformamide (100 mL) over 10% palladium on charcoal (750 mg) at 60 p.s.i. in a low pressure hydrogenation apparatus. After 90 hours, the mixture was filtered through Kieselguhr, the solvent evaporated, and the residue added to ethanol (150 mL) and acetic acid (5 mL). The mixture was heated at refux for 2 hours before addition of 10% sodium carbonate. The resultant gray solid was added to methanol (150 mL), heated to reflux, iodine (1.86 g, 7.3 mmol) added portionwise, and reflux contonued for 2 hours. Upon cooling, 10% sodium thiosulfate and 10% sodium carbonate were added until pH=8. The precipitate was collected added to methanolic hydrochloric acid (120 mL), and heated at reflux for 20 hours. Upon cooling, 10% sodium carbonate was added until pH=8, and the gray solid collected, washed with $H_2O$, methanol, and dried to afford methyl 1-(2,3-dihydro-2-oxo-1H-imidazo[4,5-b]quinolin-7-yl)-4-piperidinecarboxylate (2.14 g, 50%). An analytical sample of the title product as a partial hydrate, m.p. >310° C., was prepared by crystallization from aqueous dimethylformamide.

Anal. Calcd. for $C_{17}H_{18}N_4O_3 \cdot 0.05H_2O$: C, 62.39; H, 5.58; N, 17.12; $H_2O$, 0.28. Found: C, 62.17; H, 5.56; N, 17.05; $H_2O$, 0.24.

NMR (DMSO-$d_6$): delta 1.70–1.94 (m, 4H, piperidine C-3 and C-5 C$\underline{H}_2$), 2.50–2.90 (m, 3H, C$\underline{H}$CO$_2$CH$_3$ and NC$\underline{H}_2$), 3.64 (s, 3H, CO$_2$C$\underline{H}_3$), 3.70 (m, 2$\underline{H}$, NC$\underline{H}_2$), 7.21 (bs, 1H, C-8 Ar$\underline{H}$), 7.30 (bs, 1H, C-6 Ar$\underline{H}$), 7.45 (bs, 1H, C-9 Ar$\underline{H}$), 7.61 (bs, 1H, C-5 Ar$\underline{H}$), 10.89 and 11.29 (bs, 2$\underline{H}$, N$\underline{H}$CO).

EXAMPLE 12

1-(2,3-Dihydro-2-oxo-1H-imidazo[4,5-b]quinolin-7-yl)-4-piperidinecarboxylic Acid

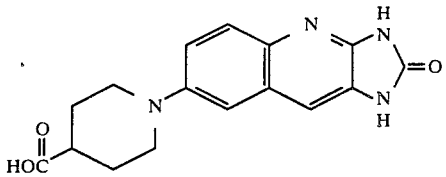

Methyl 1-(2,3-dihydro-2-oxo-1H-imidazo[4,5-b]quinolin-7-yl)-4-piperidinecarboxylate (3.4 g, 10 mmol) was added to 50% aqueous methanol (50 mL) containing 4N NaOH (5 mL, 20 mmol) and stirred for 1 hour at 24° C. The mixture was acidified to pH 5 by addition of concentrated hydrochloric acid, and the precipitate collected, washed with $H_2O$, methanol, and dried to give 1.86 g of a salmon solid (60%). The solid was suspended in hot dimethylformamide, collected, resuspended in hot methanol, and collected again to provide 1-(2,3-dihydro-2-oxo-1H-imidazo-[4,5-b]quinolin-7-yl)-4-piperidinecarboxylic Acid solvated with N,N-dimethylformamide, m.p. >310° C.

Anal. Calcd. for $C_{16}H_{16}N_4O_3 \cdot 0.25C_3H_7NO$: C, 60.85; H, 5.41; N, 18.01. Found: C, 60.68; H, 5.44; N, 18.05.

NMR (DMSO-$d_6$): delta 1.70–1.97 (m, 4H, piperidine C-3 and C-5 C$\underline{H}_2$), 2.43 (m, 1H, C$\underline{H}$CO$_2$H), 2.76–2.83 (m, 2H, NC$\underline{H}_2$), 3.68–3.72 (d, 2H, NC$\underline{H}_2$), 7.20 (s, 1H, C-8 Ar$\underline{H}$), 7.32 (d, 1H, C-6 Ar$\underline{H}$, J=9 Hz), 7.44 (s, 1H, C-9 Ar$\underline{H}$), 7.62 (d, 1H, C-5 Ar$\underline{H}$, J=9 Hz).

EXAMPLE 13

Ethyl 4-(2,3-Dihydro-2-oxo-1H-imidazo[4,5-b]quinolin-7-yl)-1-piperazinecarboxylate

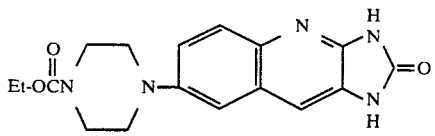

A solution of ethyl 4-[3-[(2,4-dioxoimidazolin-5-ylidene)methyl]-4-nitrophenyl]-1-piperazinecarboxylate (4.25 g, 10.9 mmol) in DMF (200 mL) was hydrogenated over 10% Pd/C (0.7 g) at 60 p.s.i. After 17 hours, the mixture was filtered through kieselguhr and the solvent removed in vacuo. Evaporation was repeated with two portions (200 mL each) of methanol. Residual solid was suspended in absolute ethanol (200 mL) and glacial acetic acid (8 mL) and stirred at reflux for one hour. The mixture was concentrated in vacuo, the residue suspended in DMF (200 mL) and warmed to solution on a steam bath. Palladium on carbon (0.5 g) was added and heating continued for two hours. The mixture was filtered through kieselguhr, the filtrate concentrated to a slurry and diluted with methanol. The precipitate was collected and crystallized from DMF to afford ethyl 4-(2,3-dihydro-2-oxo-1H-imidazo[4,5-b]quinolin-7-yl)-1-piperazinecarboxylate, a yellow solid (0.74 g) of analytical purity, m.p. >300° C.

Anal. Calcd. for $C_{17}H_{19}N_5O_3$: C, 59.81; H, 5.61; N, 20.52. Found: C, 60.17; H, 5.72; N, 20.45.

NMR (DMSO-$d_6$): delta 1.21 (3H, t, J=7 Hz, $CH_3$), 3.18 (4H, bs, $NCH_2$), 3.54 (4H, bs, $NCH_2$), 4.08 (2H, q, J=7 Hz, $OCH_2$), 7.23 (1H, d, J=2 Hz, aromatic H ortho to N), 7.33 (1H, dd, J=9 Hz, J'2 Hz, aromatic H ortho to N), 7.45 (1H, s, aromatic H ortho to NH.CO), and 7.65 (1H, d, J=9 Hz, aromatic H meta to N).

EXAMPLE 14

1-Benzoyl-4-(2,3-dihydro-2-oxo-1H-imidazo[4,5-b]quinolin-7-yl)piperazine

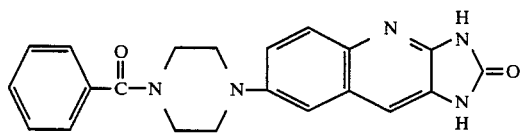

This compound, m.p. >300° C. (obtained as a methanol solvate by crystallization from dimethylformamidemethanol), was prepared analogous to Example 4 from 1-benzoyl-4-[3-[(2,4-dioxoimidazolidin-5-ylidene)methyl]-4-nitrophenyl)piperazine.

Anal. Calcd. for $C_{21}H_{19}N_5O_2 \cdot 0.25CH_4O$: C, 66.92; H, 5.28; N, 18.36. Found: C, 66.93; H, 5.19; N, 18.29.

NMR (DMSO-$d_6$): delta 3.24 (4H, bs, $NCH_2$), 3.55 (2H, bs, $NCH_2$), 3.80 (2H, bs, $NCH_2$), 7.24 (1H, s, aromatic H ortho to NH.CO), 7.34 (1H, d, J=8 Hz, aromatic H ortho to N), 7.47 (6H, s, aromatic H), and 7.65 (1H, d, J=8 Hz, aromatic H meta to N).

EXAMPLE 15

1-(2,3-Dihydro-2-oxo-1H-imidazo[4,5-b]quinolin-7-yl)-4-(3,4-dimethoxybenzoyl)piperazine

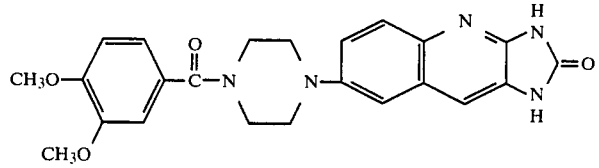

This compound, m.p. 285°-287° C. (dec.) (obtained by conversion to a hydrochloride salt and crystallization from methanol-ethanol as a partially hydrated hydrochloride salt), was prepared analogous to Example 7 from 1-(3,4-dimethoxybenzoyl)-4-[3-(2,4-dioxoimidazolidin-5-ylidene)methyl]-4-nitrophenyl]piperazine.

Anal. Calcd. for $C_{23}H_{23}N_5O_4 \cdot HCl \cdot 0.25H_2O$: C, 58.23; H, 5.21; N, 14.76; $H_2O$, 0.95. Found: C, 58.41; H, 5.12; N, 14.74; $H_2O$, 1.04.

NMR (DMSO-$d_6$): delta 3.40 to 3.72 (4H, bs, $NCH_2$), 3.80 (6H, s, $OCH_3$), 3.91 (4H, bs, $NCH_2$), 6.95 to 7.30 and 7.70 and 8.15 (7H, m, aromatic H).

EXAMPLE 16

1,3-Dihydro-7-(4-phenyl-1-piperazinyl)-2H-imidazo[4,5-b]quinolin-2-one

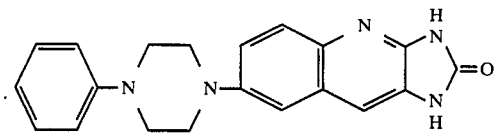

A solution of 1-[3-[(2,4-dioxoimidazolidin-5-ylidenemethyl]-4-nitrophenyl]-4-phenylpiperazine (11.13 g, 28.3 mmol) in dimethylformamide (230 mL) was hydrogenated over 10% palladium on carbon (1.5 g) at 60 p.s.i. After 16 hours the mixture was warmed to dissolve precipitated solid, filtered through kieselguhr and concentrated to a green oily residue. Methanol was added and concentrated (several times). The residue was suspended in MeOH (400 mL) containing acetic acid (20 mL) and the mixture refluxed for 18 hours. Air was bubbled into the refluxing mixture for several days with incomplete oxidation. Iodine (4.3 g, 0.017 mol) was added portionwise, refluxing continued for one hour and the cooled to room temperature. Excess iodine was quenched with 10% $Na_2S_2O_3$ and the mixture neutralized with 10% $Na_2CO_3$ solution. The mixture was concentrated to a slurry, filtered and the brown solid washed with MeOH and $H_2O$ to give 1,3-Dihydro-7-(4-phenyl-1-piperazinyl)-2H-imidazo[4,5-b]quinolin-2-one (7.55 g, 77%) which crystallized from DMF-$H_2O$ provided analytically pure material as a partial hydrate (4.2 g, 43.0%), m.p. 350°-355° C. (dec.).

Anal. Calcd. for $C_{20}H_{19}N_5O \cdot 1H_2O$: C, 69.19; H, 5.57; N, 20.17; $H_2O$, 0.52. Found: C, 68.94; H, 5.55; N, 19.96; $H_2O$, 0.48.

NMR (DMSO-d₆): delta 3.32 (8H, bs, NCH₂), 6.81 (1H, t, J=8 Hz, aromatic H), 7.50 (2H, d, J=8 Hz, aromatic H), 7.20 and 7.35 (3H, m, aromatic H), 7.38 (1H, d, J=9 Hz, aromatic H, ortho to N), 7.49 (1H, s, aromatic H ortho to NH.CO), 7.68 (1H, d, J=9 Hz, aromatic H meta or N).

EXAMPLE 17

N-Cyclohexyl-1-(2,3-dihydro-2-oxo-1H-imidazo[4,5-b]quinolin-7-yl)-N-methyl-4-piperidinecarboxamide

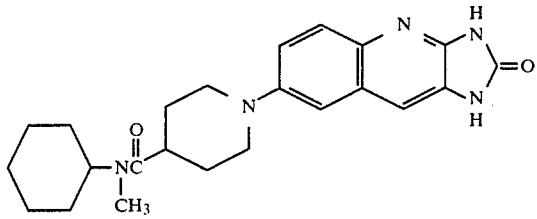

A stirred mixture of 1-(2,3-dihydro-2-oxo-1H-imidazo[4,5-b]quinolin-7-yl)-4-piperidinecarboxylic acid (3.12 g, 10 mmol) and N-cyclohexyl-N-methylamine (1.36 g, 12 mmol) were combined in dimethylformamide (200 mL) and cooled to −20° C. Triethylamine (2.91 mL, 21 mmol) and diphenylphosphoryl azide (2.59 mL, 12 mmol) were added, the mixture stirred at −20° C. for 3 hours, and allowed to warm to room temperature. After 18 hours, the mixture was diluted with CH₂Cl₂ (200 mL), scratched to initiate crystallization, and stirred for an additional 72 hours. The resultant precipitate was collected, washed with CH₂Cl₂, and dried to give 2.09 g of a pale yellow solid (51%). Crystallization from dimethylformamide (80 mL) gave 1.02 g of pale yellow crystals, m.p. 318°–321° C.

Anal. Calcd. for $C_{23}H_{29}N_5O_2 \cdot 0.33 C_3H_7NO$: C, 66.76; H, 7.31; N, 17.30. Found: C, 66.78; H, 7.33; N, 17.22.

NMR (DMSO-d₆): delta 1.09–1.72 (m, 14H, cyclohexyl —CH₂— and piperidine C-3 and C-5 —CH₂—), 2.69 and 2.87 (s, 3H, NCH₃), 2.74 and 2.89 (s, 2H, dimethylformamide), 2.77–2.83 (m, 3H, C(=O)CH and NCH₂), 3.71 and 4.25 (m, 1H, NCH), 3.77–3.80 (m, 2H, NCH₂), 7.20 (s, 1H, C-8 ArH), 7.31 (d, 1H, C-6 ArH, J=9 Hz), 7.44 (s, 1H, C-9 ArH), 7.62 (d, 1H, C-5 ArH, J=9 Hz), 7.96 (s, 0.3H, dimethylformamide), 10.88 and 11.28 (s, 2H, NHCO).

EXAMPLE 18

Methyl 1-(2,3-Dihydro-2-oxo-1H-imidazo[4,5-b]quinolin-7-yl-3-piperidinecarboxylate

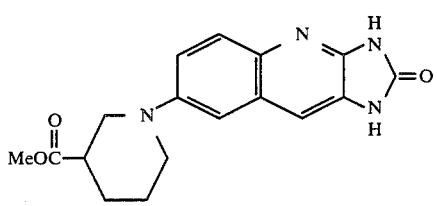

This compound is prepared analogous to Example 11 from ethyl 1-[3-[(2,4-dioxoimidazolidin-5-ylidene)methyl]-4-nitrophenyl]-3-piperidinecarboxylate.

EXAMPLE 19

N-Cyclohexyl-1-(2,3-dihydro-2-oxo-1H-imidazo[4,5-b]quinolin-7-yl)-N-methyl-3-piperidinecarboxamide

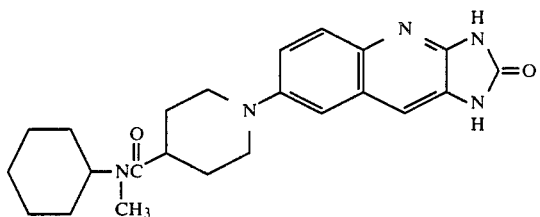

This compound is prepared analogous to Example 4 from N-cyclohexyl-1-[3-[(2,4-dioxoimidazolidin-5-ylidene)methyl]-4-nitrophenyl]-N-methyl-3-piperidinecarboxamide.

EXAMPLE 20

1,3-Dihydro-1-methyl-7-(1-piperidinyl)-2H-imidazo[4,5-b]quinolin-2-one

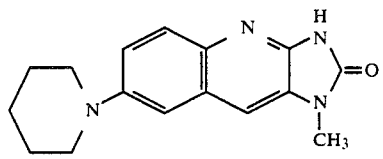

This compound is prepared analogous to Example 4 from 1-methyl-5-[[2-nitro-5-(1-piperidinyl)phenyl]methylene]-2,4-imidazolidinedione.

EXAMPLE 21

Additional Formula I Compounds

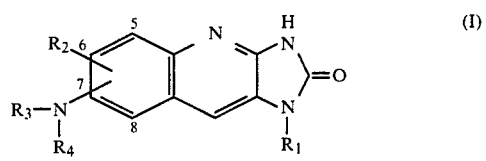

Using the procedure of Example 4 and hydantoin intermediates of Example (2–13), the following Formula I compounds wherein R₁ is hydrogen are prepared.

|     | R₂     | NR₃R₄                  |
| --- | ------ | ---------------------- |
| (a) | 8-Cl   | 7-dimethylamino        |
| (b) | 8-Cl   | 7-diethylamino         |
| (c) | 8-Cl   | 7-(1-pyrrolidinyl)     |
| (d) | 6-Cl   | 7-(1-piperidinyl)      |
| (e) | 6-Cl   | 7-dimethylamino        |
| (f) | 6-Cl   | 7-(1-piperidinyl)      |
| (g) | 6-Cl   | 7-(1-morpholinyl)      |
| (h) | 6-Me   | 7-(1-piperidinyl)      |
| (i) | 8-Cl   | 6-dimethylamino        |
| (j) | 7-Me   | 6-(1-piperidinyl)      |
| (k) | 7-MeO  | 6-(1-piperidinyl)      |
| (l) | 8-Cl   | 7-(4-phenyl-1-piperazinyl) |

What is claimed is:

1. A compound of the formula

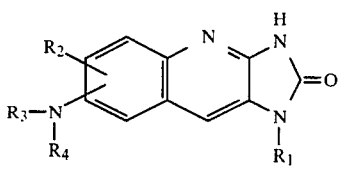

wherein

R₁ is hydrogen, lower alkyl;

R₂ is hydrogen, lower alkyl, lower alkoxy, halogen;

R₃ is hydrogen, lower alkyl;

R₄ is hydrogen, lower alkyl, alkanoyl of 1 to 6 carbon atoms, phenylalkanoyl of 7 to 10 carbon wherein phenyl is optionally substituted with halogen, lower alkyl, or lower alkoxy;

R₃ and R₄ are joined together to form 1-morpholinyl, 1-piperidinyl or 1-pyrrolidinyl optionally substituted with —CO₂R₅ or

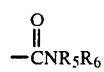

wherein R₅ is hydrogen or lower alkyl, and R₆ is hydrogen, lower alkyl, cycloalkyl of 5 to 7 carbon atoms; 1-(4-R₇-piperazinyl) wherein R₇ is —CO₂R₈ wherein R₈ is lower alkyl; phenyl optionally substituted with up to 2 halogen, lower alkyl or lower alkoxy; R₇ may also be phenylalkanoyl of 7 to 10 carbon atoms wherein phenyl is unsubstituted or independently substituted with up to 2 halogen, lower alkyl, lower alkoxy;

or a pharmaceutically acceptable salt thereof.

2. The compound of claim 1 or a pharmaceutically accpetable salt thereof which is N-(2,3-dihydro-2-oxo-1H-imidazo[4,5-b]quinolin-7-yl)acetamide.

3. The compound of claim 1 or a pharmaceutically acceptable salt thereof which is 7-amino-1,3-dihydro-2H-imidazo[4,5-b]quinolin-2-one.

4. The compound of claim 1 or a pharmaceutically acceptable salt thereof which is N-(2,3-dihydro-2-oxo-1H-imidazo[4,5-b]quinolin-7-yl)benzamide.

5. The compound of claim 1 or a pharmaceutically acceptable salt thereof which is 1,3-dihydro-7-(1-piperidinyl)-2H-imidazo[4,5-b]quinolin-2-one.

6. The compound of claim 1 or a pharmaceutically acceptable salt thereof which is 1,3-dihydro-7-(1-pyrrolidinyl)-2H-imidazo[4,5-b]quinolin-2-one.

7. The compound of claim 1 or a pharmaceutically acceptable salt thereof which is 7-(diethylamino)-1,3-dihydro-2H-imidazo[4,5-b]quinolin-2-one.

8. The compound of claim 1 or a pharmaceutically acceptable salt thereof which is 1,3-dihydro-7-(4-morpholinyl)-2H-imidazo[4,5-b]quinolin-2-one.

9. The compound of claim 1 or a pharmaceutically acceptable salt thereof which is methyl 1-(2,3-dihydro-2-oxo-1H-imidazo[4,5-b]quinolin-7-yl)-4-piperidinecarboxylate.

10. The compound of claim 1 or a pharmaceutically acceptable salt thereof which is 1-(2,3-dihydro-2-oxo-1H-imidazo[4,5-b]quinolin-7-yl)-4-piperidinecarboxylic acid.

11. The compound of claim 1 or a pharmaceutically acceptable salt thereof which is ethyl 4-(2,3-dihydro-2-oxo-1H-imidazo[4,5-b]quinolin-7-yl)-1-piperazinecarboxylate.

12. The compound of claim 1 or a pharmaceutically acceptable salt thereof which is 1-benzoyl-4-(2,3-dihydro-2-oxo-1H-imidazo[4,5-b]quinolin-7-yl)piperazine.

13. The compound of claim 1 or a pharmaceutically acceptable salt thereof which is 1-(2,3-dihydro-2-oxo-1H-imidazo[4,5-b]quinolin-7-yl)-4-(3,4-dimethoxybenzoyl)piperazine.

14. The compound of claim 1 or a pharmaceutically acceptable salt thereof which is 1,3-dihydro-7-(4-phenyl-1-piperazinyl)-2H-imidazo[4,5-b]quinolin-2-one.

15. The compound of claim 1 or a pharmaceutically acceptable salt thereof which is N-cyclohexyl-1-(2,3-dihydro-2-oxo-1H-imidazo[4,5-b]quinolin-7-yl)-N-methyl-4-piperidinecarboxamide.

16. A method for inhibiting phosphodiesterase in a mammal which comprises administering a therapeutically effective amount of a compound of claim 1 or a pharmaceutically acceptable salt thereof.

17. The pharmaceutical composition for inhibiting phosphodiesterase comprising a therapeutically effective amount of a compound of claim 1 or a pharmaceutically acceptable acid addition salt thereof and a pharmaceutical carrier.

18. The pharmaceutical composition comprising a therapeutically effective amount of a compound of claim 1 or a pharmaceutically acceptable acid addition salt thereof and a pharmaceutical carrier.

19. A method for inhibiting blood platelet aggregation in a mammal which comprises administering a therapeutically effective amount of a compound of claim 1 or a pharmaceutically acceptable salt thereof.

20. The pharmaceutical composition for inhibiting blood platelet aggregation comprising a therapeutically effective amount of a compound of claim 1 or a pharmaceutically acceptable acid addition salt thereof and a pharmaceutical carrier.

* * * * *